(12) United States Patent
Bastide et al.

(10) Patent No.: US 10,751,698 B2
(45) Date of Patent: Aug. 25, 2020

(54) METHOD FOR THE PURIFICATION OF WHOLE BLOOD OR A BLOOD-DERIVED PRODUCT

(71) Applicants: ELICITYL, Crolles (FR); RESEARCH FOUNDATION FOR MEDICAL DEVICES, Fribourg (CH)

(72) Inventors: Ludovic Bastide, Les Adrets (FR); Silvère Bonnet, Grenoble (FR); Benoît Darblade, Crolles (FR); Stéphane Havet, Gieres (FR); Bernard Mandrand, Villeurbanne (FR); Mialy Randriantsoa, Grenoble (FR); Jean-Philippe Zeris, Saint Cyr au mont d'Or (FR)

(73) Assignees: ELICITYL, Crolles (FR); RESEARCH FOUNDATION FOR MEDICAL DEVICES, Fribourg (CH)

( * ) Notice: Subject to any disclaimer, the term of this patent is extended or adjusted under 35 U.S.C. 154(b) by 283 days.

(21) Appl. No.: 15/571,273

(22) PCT Filed: May 3, 2016

(86) PCT No.: PCT/FR2016/051044
§ 371 (c)(1),
(2) Date: Nov. 2, 2017

(87) PCT Pub. No.: WO2016/177966
PCT Pub. Date: Nov. 10, 2016

(65) Prior Publication Data
US 2018/0345250 A1    Dec. 6, 2018

(30) Foreign Application Priority Data

May 6, 2015    (FR) .................................... 15 54084

(51) Int. Cl.
*B01J 20/32*      (2006.01)
*B01D 15/38*      (2006.01)
(Continued)

(52) U.S. Cl.
CPC ........ *B01J 20/3212* (2013.01); *A61M 1/0281* (2013.01); *A61M 1/3679* (2013.01);
(Continued)

(58) Field of Classification Search
CPC .... B01D 15/08; B01D 15/38; B01D 15/3804; B01D 15/3809; B01D 15/02; B01D 15/18;
(Continued)

(56) References Cited

U.S. PATENT DOCUMENTS 3,555,143 A    1/1971    Axen et al.
3,947,352 A *  3/1976    Cuatrecasas ............. B01J 20/22
                                                    210/692
(Continued)

FOREIGN PATENT DOCUMENTS

DE    199 53 590    5/2001
EP    0 131 546    1/1985
(Continued)

*Primary Examiner* — Katherine Zalasky McDonald
(74) *Attorney, Agent, or Firm* — Clark & Brody LP

(57)    ABSTRACT

The present invention concerns a method of purifying a biological liquid comprising antibodies corresponding to whole human or animal blood or to a product obtained from human or animal blood, by bringing a biological liquid into contact with at least one substrate comprising a solid phase onto which molecules of at least one oligosaccharide are grafted by covalent bonding, the molecules of the at least one oligosaccharide being capable of binding to one or more of said antibodies present in said biological liquid, in a manner such as to capture at least a portion of said antibodies present in said biological liquid by binding with at least (Continued)

certain of the molecules of oligosaccharide(s) grafted onto said solid phase, characterized in that said solid phase carries free aldehyde functions —CHO.

27 Claims, 2 Drawing Sheets

(51) Int. Cl.
    *A61M 1/36*     (2006.01)
    *B01J 20/286*     (2006.01)
    *A61M 1/02*     (2006.01)
    *G01N 33/49*     (2006.01)
    *A61K 35/16*     (2015.01)
(52) U.S. Cl.
    CPC ..... *B01D 15/3804* (2013.01); *B01D 15/3809* (2013.01); *B01J 20/286* (2013.01); *B01J 20/3219* (2013.01); *B01J 20/3274* (2013.01); *B01J 20/3278* (2013.01); *G01N 33/491* (2013.01); *A61K 35/16* (2013.01)
(58) Field of Classification Search
    CPC ........ B01J 20/22; B01J 20/285; B01J 20/289; B01J 20/286; B01J 20/32; B01J 20/3274; B01J 20/3208; B01J 20/28016; B01J 20/3212; B01J 20/3217; B01J 20/3219; B01J 20/3242; B01J 20/3278; G01N 30/02; G01N 30/60; A61M 1/0281; A61M 2202/0057; A61M 2202/0021
    See application file for complete search history.

(56) References Cited

U.S. PATENT DOCUMENTS

| | | | |
|---|---|---|---|
| 4,108,974 A | 8/1978 | Wegfahrt et al. | |
| 4,238,473 A | 12/1980 | Lemieux et al. | |
| 4,664,913 A | 5/1987 | Mielke et al. | |
| 5,059,654 A * | 10/1991 | Hou | A61K 39/39525 210/198.2 |
| 5,407,581 A * | 4/1995 | Onodera | B01D 39/1623 210/321.69 |
| 5,460,945 A * | 10/1995 | Springer | A61M 1/3679 422/533 |
| 5,496,937 A * | 3/1996 | Okamoto | C07B 57/00 210/198.2 |
| 5,567,615 A * | 10/1996 | Degen | B01D 29/01 435/280 |
| 2004/1242857 | 12/2004 | Nilsson | |
| 2006/0068369 A1 * | 3/2006 | Coelho | A61M 1/0272 435/2 |
| 2009/0074749 A1 * | 3/2009 | Chtourou | C07K 16/34 424/130.1 |
| 2009/0216006 A1 * | 8/2009 | Xu | C08B 15/06 536/55.3 |
| 2010/0221844 A1 * | 9/2010 | Bian | B01D 15/3809 436/501 |
| 2012/0219633 A1 * | 8/2012 | Sowemimo-Coker | A61K 35/14 424/535 |
| 2014/0166580 A1 * | 6/2014 | Rempfer | B01J 20/26 210/650 |
| 2014/0284274 A1 * | 9/2014 | Nilsson | B01D 63/02 210/638 |
| 2015/0111194 A1 * | 4/2015 | Rempfer | B01J 20/26 435/2 |
| 2015/0133636 A1 * | 5/2015 | Xenopoulos | B01D 15/362 530/387.1 |
| 2015/0344520 A1 * | 12/2015 | Matsumoto | C07K 1/22 530/413 |
| 2017/0066839 A1 * | 3/2017 | Bian | C07K 16/34 |
| 2017/0067914 A1 * | 3/2017 | Stone | G01N 33/80 |
| 2017/0067915 A1 * | 3/2017 | Rahane | C07K 1/22 |
| 2018/0080858 A1 * | 3/2018 | Richter | B01D 15/3823 |

FOREIGN PATENT DOCUMENTS

| | | |
|---|---|---|
| EP | 0 435 470 | 7/1991 |
| EP | 0 572 194 | 12/1993 |
| EP | 0 896 824 | 2/1999 |
| EP | 2 556 848 | 2/2013 |
| FR | 2 796 082 | 1/2001 |
| FR | 3 008 097 | 1/2015 |
| WO | 01/04341 | 1/2001 |
| WO | 01/58510 | 8/2001 |
| WO | 2008/136735 | 11/2008 |
| WO | 2011/046504 | 4/2011 |

* cited by examiner

METHOD FOR THE PURIFICATION OF WHOLE BLOOD OR A BLOOD-DERIVED PRODUCT

FIELD OF THE INVENTION

The present invention relates to the field of purifying blood and products obtained from blood and in particular to the purification of plasma by eliminating the antibodies present. More precisely, the invention relates to a method of purifying a biological liquid corresponding to whole human or animal blood or to a product obtained from human or animal blood using a particular substrate carrying at least one type of oligosaccharide, in particular a determinant of the blood groups.

BACKGROUND OF THE INVENTION

The immune system is a defence mechanism of the organism having the function of protecting an organism from foreign attacks. The response known as the humoral response produces antibodies with a repertoire that is unique to each individual. However, the immune system, in particular the antibodies secreted by the humoral response, are the source of major risks when transplanting animal tissue or organs into human beings or during inter-human transfers (of blood, plasma or an organ).

Similarly, many auto-immune diseases are due to the perception by the organism of the organism's own protein, lipid, or saccharide determinants as being foreign, which generates a chronic immune response. Similarly, when pharmaceutical preparations containing antibodies are injected into an individual, it is vital that the corresponding antigen, if it is not the therapeutic target, is not present in the recipient in order to avoid the risk of causing an unwanted response; one example of such a response is hemolysis due to antibodies against the antigenic determinants of the blood groups. Thus, an injectable preparation must be free from that type of antibody.

To accomplish this, anti-protein antibodies have been purified for a long time, but purifying anti-saccharide antibodies is more problematic because of the difficulty of synthesizing the antigens (which are complex molecules resulting from a multi-enzymatic in vivo synthesis) and of the low affinity constant between the antibody and the antigen. This low affinity of the anti-saccharide antibodies leads to the presence of a very large excess of antigen compared with the antibodies that are to be eliminated from the medium (the excess is by a very large factor, i.e. 10000 to 100000 molecules of saccharide antigen for one molecule of antibody, this ratio being reduced if the oligosaccharide is bound onto a solid multimerized or polymerized phase). At the same time, the affinity of an IgM type antibody, which is a multimer with 10 possibilities for binding to the antigen via molecules, is higher than that for IgGs that only have two binding sites to the antigen. In the case of IgMs, this is known as avidity in order to take into account the synergistic effect of multiple antibody functions.

Thus, it is important to use substrates multimerizing the saccharide antigens and to adapt them to the purification of IgGs as well as IgMs.

The separation of anti-saccharide antibodies, which are considered to be undesirable, from a biological liquid while conserving all of its properties, is a major therapeutic advance that has many applications.

During a blood transfusion, in order to be universal, the transfused plasma must be freed from antibodies that are known or assumed to be from the donor. Transfusions of biological liquids such as plasma are therapeutic acts for the purpose of obtaining regeneration of the hemostatic system or restoring the hemodynamics of the patient. The presence of antibodies from a donor with an incompatible group is tantamount to endangering the recipient patient by generating a hemolytic shock. The antibodies of blood groups present in the donor's plasma (anti-A, anti-B or both depending on the blood group) are determined by saccharide elements. In the current care system, a patient will only receive blood products that are identical to or compatible with that patient's blood group, giving rise to high logistical and storage costs. Proposing a plasma that is compatible with all patients would constitute a safe and economical solution.

Similarly, during a xeno-graft (i.e. a graft of an animal organ into a human), the antibodies against the determinants of the grafted organ must be eliminated in order to prevent massive rejection of the organ. Immunosuppressor treatment is a therapeutic solution to the problem, but suffers from secondary effects that can be life-threatening to the patient, and thus it is not entirely effective. Neutralization of the xeno-antibodies in the recipient by binding to the xeno antigens, which are saccharide compounds, constitutes an advantage in the field of xeno-grafts.

In autoimmune diseases, the excess of auto-antibodies may have important consequences. As an example, in Guillain Barré syndrome, the patient's auto-antibodies attack the patient's own nervous system and destroy the peripheral nerves (sometimes right up to the axon). It has been demonstrated that these antibodies become bound to gangliosides (which have a saccharidic antigen determinant) present in the nervous system. The motif that is recognised is also a saccharide. Being able to eliminate those elements that are not controlled from the immune system is an avenue for treatment of the syndrome.

More precisely, with blood transfusions, the key elements of the blood, red blood cells, platelets, and lymphocytes, carry A, B, or H saccharide antigens on their surface, which determine the blood group of individuals in a primate species. Individuals in blood group A have group A antigens; individuals in blood group B have group B antigens; individuals in blood group AB have both types of antigens. Individuals in blood group O carry the H antigen of which the oligosaccharide concatenation is found in group A and B antigens. A and B antigens have a supplemental monosaccharide. Group A antigens and group B antigens are also carried by various non-pathogenic infectious agents, essentially bacteria. Very early contact with such infectious agents brings about an immune response against the A or B determinant that the individual does not carry. Thus, individuals with blood group A mount a plasma response by generating anti-determinant B antibodies (also known as anti-B) and individuals with group B mount a plasma response by generating anti-determinant A antibodies (also known as anti-A); AB individuals do not have antibodies and those in group O have anti-A and anti-B antibodies. Blood group antibodies are essentially of the IgG and IgM type.

Plasma taken by plasmapheresis or from whole blood can only be used to treat patients after blood typing and plasma typing of the patients; this introduces a risk of errors, is time-consuming, and is a source of considerable logistical complexity.

In order to overcome this disadvantage, several solutions have been proposed. Mixing plasmas in defined proportions can dilute the concentrations of antibodies and can provide a mixture of antigens and antibodies that are mutually neutralizing (EP 0 896 824). However, thiat solution is only partial because the effective mixtures do not correspond to the frequency of the desired groups in donor populations. This solution is also risky since it leaves immune complexes in the treated plasmas, which are a potential source of autoimmune reactions.

A number of solutions also propose eliminating the antibodies from the plasma using group A or B-determinant antigenic oligosaccharides. One of the first to propose a solution of this type was Raymond U. Lemieux (U.S. Pat. No. 4,238,473 published in 1980). Since then, a number of approaches using chromatographic techniques in particular have been proposed, but have not been satisfactory in terms of efficiency and/or cost. The following may be cited in particular:

- patent application EP 0 572 194, which describes a method of eliminating antibodies from a blood product while preserving the coagulation factors (see claim 1). To this end, a matrix is described that is constituted by a resin carrying antigens that may be bound by covalent bonding. Those antigens may be oligosaccharides. No detail is given as regards the modes by which the antigens are bound to the matrix;
- U.S. Pat. No. 4,664,913, which describes a method of treating human plasma by passage through an immunoadsorbing zone that is capable of binding both anti-A and anti-B antibodies. The antigen/substrate bond in the immunoadsorbing zone is produced by reaction of an acyl azide function carried by the antigen on an aminated substrate. Reference is also made in that document both to U.S. Pat. No. 3,555,143, which describes particles carrying amine, carboxy, or hydroxy functions in order to bind to the antibodies, and also to patent U.S. Pat. No. 4,108,974, which describes beads carrying carboxylate for coupling with antibodies carrying amine functions;
- document WO 2008/136735, which concerns a substance comprising at least one ligand, bound to a separation material, also termed a matrix, allowing for selective binding to a biomolecule or selective cleavage of a biomolecule. One of the applications for that product is its use to reduce the antibodies in a plasma or in a sample of whole blood. Binding to the matrix is envisaged via an $NH_2$ function located at the end of the spacer arm located at the end of the saccharide, in particular on epoxy-activated agarose, tosyl-activated agarose, or a CnBr-activated matrix;
- patent application EP 1 165 159, which describes a particular configuration of columns for the treatment of whole blood or of blood plasma, which contains a cross-linked matrix material to which at least one biologically active saccharide is covalently bound via at least one specific spacer. The binding mode described uses the reaction of an oligosaccharide carrying an —$NH_2$ function at the end of the spacer arm on activated Sepharose-NHS. Other types of substrate of the epoxy-activated Sepharose type are cited. No other example of coupling is provided in the description;
- patent application WO 2011/046504, which describes a product and a method for carrying out a treatment or a purification containing at least two filters or one filter and one centrifugation or two centrifugations and a component that contains at least one substance that is capable of binding to a target substance. It is pointed out that the ligand is bonded to the matrix in a covalent manner and that various methods selected by the person skilled in the art could be used. The binding mode detailed uses covalent coupling between an —$NH_2$ function carried by the saccharide, and a carbonyl group present on the matrix in order to obtain an amide bond is described. It is also pointed out that the amide bond may be obtained by the EDC/NHS (1-ethyl-3-(3-dimethylaminopropyl)carbodiimide and N-hydroxysuccinimide) reaction with a carboxyl group on the matrix that is activated in order to react with the saccharide derivative. A more precise example is not provided;
- patent application EP 2 556 848, which describes a separation material comprising a saccharide bonded via a particular spacer arm to a matrix in order to be able to separate substances from a liquid. It is pointed out that the oligosaccharide-matrix bond may be obtained by reacting a compound on a matrix carrying —$NH_2$, —$N_3$, —COOH, —CHO, $NH_2$—NH—, HCC— or epoxy functions (see definition of $F^1$ on page 4, line 7). The coupling reaction detailed in paragraph [0069] states that the bond is formed between a carboxyl group and an amine and that one of the methods conventionally used is the reaction of a carboxylic acid with a carbodiimide in order to facilitate its coupling with an amine in a manner such as to obtain an amide type bond. The substrates detailed in the examples exclusively incorporate epoxy, amino, and carboxylic acid functions.

Thus, it appears that various solutions using antigenic oligosaccharides of a blood group grafted onto a substrate have been proposed. The oligosaccharide/substrate bond is usually produced on a substrate carrying —$NH_2$, epoxy, or carboxylic acid functions.

SUMMARY OF THE INVENTION

In the context of the invention, a purification method is proposed that uses a novel substrate, in particular in order to favour binding of IgG and IgM type antibodies onto binding partners of an oligosaccharide nature, and in particular the binding of antibodies of blood groups.

The present invention provides a purification method for purifying a biological liquid corresponding to whole human or animal blood or to a product obtained from human or animal blood comprising antibodies, by bringing a biological liquid into contact with at least one substrate comprising a solid phase onto which molecules of at least one oligosaccharide that is capable of binding to one or more of said antibodies present in said biological liquid are grafted by covalent bonding, in a manner such as to obtain the capture of at least a portion of said antibodies present in said biological liquid by binding with at least some of the molecules of oligosaccharide(s) grafted onto said solid phase, characterized in that said solid phase carries free aldehyde functions —CHO.

In the context of the invention, the free aldehyde functions —CHO stabilize the antibodies following their immunological recognition by said molecules of oligosaccharide(s) grafted onto the solid phase. The free aldehyde functions —CHO are distributed over the solid phase and interact with the antibodies initially contained in the biological liquid to be purified and that will bind by immuno-affinity binding onto the molecules of oligosaccharide(s) grafted onto the solid phase. In particular, the stabilization of the oligosaccharide/antibodies bond is obtained by bonding, in particular by covalent bonding, with one or more of the following amino acids: asparagine, lysine, arginine, glutamine, tyrosine, tryptophan, or cysteine, present on said antibody, onto a free aldehyde function present on the solid phase. The free aldehyde functions, —CHO are present directly on the solid phase and not at all on the oligosaccharides.

In addition, advantageously, in the purification method in accordance with the invention, said at least one substrate is used, by means of at least a portion of the free aldehyde functions present on the solid phase, to ensure stabilization of the antibodies, and in particular of the IgGs, which will become bound to at least certain of the molecules of oligosaccharide(s) grafted onto said solid phase. The free aldehyde functions, —CHO can interact with the antibodies and stabilize their affinity bond to the purification substrate.

In the purification methods in accordance with the invention, a substrate is used that comprises a solid phase onto which there are grafted, by covalent bonding, molecules of at least one oligosaccharide that is capable of binding to one or more antibodies present in said biological liquid that is to be purified, said solid phase being a carrier of free aldehyde functions —CHO. Substrates of this type, termed "substrates" in the present patent application for the purposes of simplification, is described below in detail.

DETAILED DESCRIPTION OF THE INVENTION

Solid Phases Used

Figure 1:
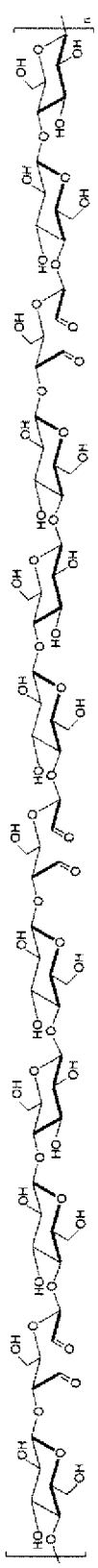
FIG. 1 illustrates the generation of aldehyde functions in the case of cellulose, by periodic oxidation involving cleavage of a C—C bond between the two carbons carrying the two neighboring alcohols of a saccharide unit and generating two aldehyde functions, The generation of aldehyde functions in a regular manner every four glucoside units is shown.

Various types of solid phases may be used in the substrates employed in the context of the invention. In particular, a solid phase will be used that is insoluble in an aqueous phase. Examples of solid phases that may be cited are solid phases of an organic nature, in particular of the polymeric, plastic, polysaccharide or protein, etc. type, such as polystyrene, polycarbonates, polyacrylates, polysulfones, polyurethanes, cellulose, agarose, dextran, chitosan, polylysine, or in fact solid phases that are of an inorganic nature, such as silica or alumina. The solid phase may be in the particular form of particles or a fibrous matrix or a solute that may be rendered insoluble or selectively separated.

In the context of the invention, the solid phase has been selected to allow the aminated oligosaccharides, which are easier to purify, to be grafted. In the prior art, grafting of aminated oligosaccharides was carried out on solid phases carrying epoxy or carboxylic acid functions. Those prior art techniques have disadvantages compared to those preferred in the context of the invention: epoxy amine grafting is difficult to control and grafting onto a carboxylic acid involves EDC and/or NHS molecules that make the coupling reaction more complex.

In the context of the invention, the solid phase carries free aldehyde functions: these functions in particular correspond to residual aldehyde functions remaining on the solid phase after grafting molecules of oligosaccharide(s), grafting of which being carried out onto other aldehyde functions that are initially present on the surface of the solid phase.

In addition, advantageously, in the substrates used in accordance with the invention, the molecules of oligosaccharide(s) are grafted onto a solid phase carrying free aldehyde functions —CHO by reaction of an oligosaccharide carrying a reactive function that is capable of forming a covalent bond with said aldehyde functions —CHO on only a portion of the free aldehyde functions —CHO present on the solid phase. This grafting reaction is carried out in a manner such that in the end, free aldehyde functions subsist on the solid phase. The covalent bond existing between the solid phase and the molecules of oligosaccharide(s) grafted onto the final substrate preferably corresponds to a bond resulting from the reaction of an amine function of the —NH$_2$, —NH—NH$_2$, or —O—NH$_2$ type, optionally in a protected form, carried by the oligosaccharide before grafting and an aldehyde function —CHO carried by the solid phase before grafting.

The free aldehyde functions are thus introduced onto the solid phase before grafting the molecules of oligosaccharide and will be a function of the nature of said solid phase. As an example, the aldehyde functions could be inserted directly during polymerization of the solid phase.

It is also possible for the solid phase to contain one or more types of reactive functions that will allow the free aldehyde functions to be introduced. In particular, the solid phase may contain one or more types of reactive functions with an electrophilic nature, such as carboxylic acids and activated derivatives (for example, carboxylic acids activated with NHS), epoxies, isocyanates, and isothiocyanates. These functions could be derived from the aldehyde by reaction with a reagent which, firstly, carries a thiol, an alcohol, a —NH$_2$, —NH—NH$_2$, or —O—NH$_2$ function, and secondly carries a masked aldehyde function such as an acetal. The aldehyde function could then be deprotected by hydrolysis of the acetal. As an example, it would be possible to graft aminoacetaldehyde dimethyl acetal by reacting its amino function onto a solid phase carrying epoxy functions. The aldehyde will then be liberated in an acidic solution.

Alternatively, the solid phase may contain one or more types of reactive functions having a nucleophilic nature, such as thiols, alcohols, and the functions —NH$_2$, —NH—NH$_2$ and —O—NH$_2$. A reactive function of this type could either be reacted with a molecule having firstly an acid function that will be activated to form an amide bond with the solid phase, and secondly a masked aldehyde function, or with a molecule with two aldehyde functions such as glutaraldehyde or dimethoxyethanal, this latter then having to undergo a deprotection step.

Alternatively, the solid phase may contain hydroxyl functions that could also be deprotonated by a strong base and brought into the presence of a reagent which firstly carries a halogen of the chlorine type and secondly carries a masked aldehyde function such as an acetal, such as dimethyl acetal halogen acetaldehyde. This results in a masked aldehyde function bonded to the solid phase via an ether bond. This function will then be deprotected to the aldehyde. This same type of hydroxylated polymer may be activated by cyanogen bromide that could then also react with the amine of the dimethyl acetal aminoacetaldehyde.

With a mineral solid phase such as silica, this latter could be functionalized by a trichlorosilane, trimethoxysilane or triethoxysilane also comprising a reactive function, aldehyde or otherwise, which could then be derivatized into an aldehyde, for example (3-glycidyloxypropyl) trimethoxysilane.

Irrespective of the nature of the solid phase (organic or inorganic), it is also possible to use a solid phase carrying functions that are reactive in "click chemistry", in order to introduce the free aldehyde functions. Examples of such functions that are reactive in "click chemistry" are selected from thiol, maleimide, allyl, acrylate, azide, propargyl, etc. functions, which could be reacted with a corresponding reagent that is capable of introducing a free aldehyde function by "click chemistry".

Advantageously, the substrate used in accordance with the invention comprises a solid phase in the form of hydrophilic particles of the cellulose type. A selection of this type means that the proteins of a purified biological liquid can be concentrated using said substrate.

In the context of the invention, a solid phase of cellulose is preferably used. Cellulose has the advantage of being a cheap solid phase which, in addition, because of its absorbing power, can be used to concentrate biological liquids such as the products obtained from blood and in particular plasma, which is to be purified with the substrate in accordance with the invention, thereby retaining a portion of the water contained in said biological liquids.

In fact, a solid phase such as cellulose has the advantage of being readily dispersed in the medium to be treated (blood or product obtained from blood), of offering a large accessible surface area, and of having good chemical and immunological neutrality in respect of the components of human blood. Using it, preferably in the form of stable and aseptic particles, does not involve dilution of the plasma proteins. In fact, concentration of the plasma proteins is a sought-after effect.

In the context of the invention, it would in particular be possible to use a micronized cellulose or a microcrystalline cellulose as the solid phase.

Microcrystalline cellulose is obtained by controlled mechanical disintegration and acid hydrolysis of the ends starting from micronized cellulose that is itself obtained by mechanical disintegration from pulping fibrous cellulosic plant material. The fibrous ends present on the micronized cellulose are eliminated on microcrystalline cellulose, which is more compact.

In the case of a solid phase selected from polysaccharides, and in particular in the case of cellulose, the aldehyde functions could be introduced onto the solid phase by periodic oxidation, TEMPO oxidation (2,2,6,6-tetramethylpiperidine-1-oxyl), Swern oxidation, etherification with a masked halogenated aldehyde, derivitization of cellulose into tosylate (—OTs) (on which the alcoholate of dimethyl acetal glycoladehyde or a —NH$_2$ is reacted by substitution), CNBr activation (followed by reaction with dimethyl acetal aminoacetaldehyde). In the case of acetals formed as intermediates, they are then hydrolysed to produce a free aldehyde function.

More particularly, periodic oxidation involves cleavage of a C—C bond between the two carbons carrying the two neighboring alcohols of a saccharide unit and generating two aldehyde functions. FIG. 1 illustrates the generation of such aldehyde functions in the case of cellulose. Two aldehyde functions close to each other are thus generated. The generation of aldehyde functions in a regular manner every four glucoside units as shown in FIG. 1 is given purely by way of illustration. The aldehyde functions could be generated in a regular or randomized manner and at any separation from each other. In addition, advantageously, in the substrates in accordance with the invention, the solid phase is a polysaccharide and the free aldehyde functions result from a periodic oxidation. Yet more preferably, in the substrates in accordance with the invention, the solid phase is cellulose that comprises units with formula:

—CH(—CHO)—CH(CH$_2$OH)—O—CH(—CHO)—O—.

In fact, certain of these units may exist in the solid phase carrying the grafted molecules of oligosaccharide.

The conditions used for the introduction of the aldehyde functions, and in particular periodic oxidation, may be adapted by the person skilled in the art as a function of the desired density of the aldehyde functions to be introduced onto the solid phase.

Reference may in particular be made to "An introduction to the chemistry of carbohydrates", R. D. Guthrie & John Honeyman, Oxford University Press, 1968, page 108 to 112, for the conditions to be applied for the periodic oxidation of cellulose or, more generally, polysaccharides. In particular, with periodic oxidation, a periodate such as sodium metaperiodate NaIO$_4$ will be used. The periodic oxidation reaction will usually be carried out in the solid phase taken up into suspension in a solvent.

As an example, sodium metaperiodate NaIO$_4$ dissolved in an aqueous phase is reacted on a solid phase of the polysaccharide type such as cellulose in suspension. Advantageously, the reaction is carried out with stirring, preferably in the absence of light, with or without heating, and preferably at a temperature in the range from 0° C. to 30° C., preferably in a neutral or acidic medium. The quantity of free aldehyde functions introduced onto the solid phase of the polysaccharide type such as cellulose depends in particular on the concentration of reagent used, and in particular of oxidizing agent such as sodium metaperiodate, NaIO$_4$. The conditions will be adapted in order to obtain, as is preferable, one aldehyde function per 100 to 4 saccharide monomers, preferably one aldehyde function per 25 to 8 saccharide monomers.

Solid phases already carrying free aldehyde functions, in particular in the form of formyl groups, are also commercially available. Activated macroporous chromatographic solid phases of a methacrylic polymer sold by Tosoh Biosciences, in particular with the reference Toyopearl AF-Formyl-650, or agarose gels carrying aldehyde functions may in particular be cited. A solid phase of this type carrying free aldehyde functions is then ready to be functionalized by covalent grafting of molecules of oligosaccharide(s) onto a portion of the aldehyde functions.

Oligosaccharide and Grafting Onto the Solid Phase

It is possible for molecules of a single oligosaccharide or molecules of several different oligosaccharides to be grafted onto the solid phase.

The oligosaccharide or oligosaccharides grafted onto the solid phase is(are) qualified as antigenic due to their capacity to recognize one or more antibodies.

The oligosaccharide or oligosaccharides is(are) preferably a trisaccharide, a tetrasaccharide, a pentasaccharide or a hexasaccharide.

In the context of the invention, molecules of at least one oligosaccharide that is capable of binding to anti-determinant A, B, or H antibodies of the blood groups are preferably grafted onto the solid phase. Anti-determinant A antibodies are regular antibodies present in human beings with blood group B or O; anti-determinant B antibodies are regular antibodies present in human beings with blood group A or O; anti-determinant H antibodies are antibodies present in certain human beings with blood group O. The oligosaccharides present on the substrates in accordance with the invention, which are capable of binding to the anti-determinant antibodies of the blood group may be of any type: antigenic oligosaccharide of determinant A, antigenic oligosaccharide of determinant B in particular, for example in their natural hexasaccharide or reduced size form (tri-, tetra- or penta-saccharide).

In particular, the grafted oligosaccharide or oligosaccharides could be selected from oligosaccharides that are capable of binding to anti-determinant B antibodies, present in individuals with blood group A or O, such as the type 5 tetrasaccharide that is not present in the human repertoire but which, surprisingly, has an excellent affinity for human antibodies, the type 1 hexasaccharide and type 2 hexasaccharide, which form part of the human repertoire; among the oligosaccharides that are capable of binding to anti-determinant A antibodies present in individuals with blood group B or O such as the type 5 tetrasaccharide that is not present in the human repertoire but which, surprisingly, has an excellent affinity for human antibodies, type 1 hexaose and type 2 hexaose that form part of the human repertoire.

Advantageously, the substrate used in accordance with the invention will carry molecules of an oligosaccharide that is capable of binding to anti-determinant B antibodies present in individuals with blood group A or O and/or molecules of an oligosaccharide that is capable of binding to anti-determinant A antibodies present in individuals with blood group B or O. Examples of such oligosaccharides that may be cited are as follows: GalNAcα1-3(Fucα1-2)Galβ1, Galα1-3 (Fucα1-2)Galβ1, GalNAcα1-3(Fucα1-2)Galβ1-4Glc, Galα1-3(Fucα1-2)Galβ1-4Glc, GalNAcα1-3(Fucα1-2) Galβ1-3GlcNAcβ1-3Galβ1-4Glc, Galα1-3(Fucα1-2) Galβ1-3GlcNAcβ1-3Galβ1-4Glc, GalNAcα1-3(Fucα1-2) Galβ1-4GlcNAβ1-3Galβ1-4Glc, and Galα1-3(Fucα1-2) Galβ1-4GlcNAcβ1-3Galβ1-4Glc, Fucα1-2Galβ1-3GlcNAc, Fucα1-2Galβ1-4GlcNAc, Fucα1-2Galβ1-4Glc, Fucα1-2Galβ1-3GlcNAcβ1-3Gal, Fucα1-2Galβ1-4GlcNAcβ1-3Gal, Fucα1-2Galβ1-3GalNAcβ1-3Gal, Fucα1-2Galβ1-3GlcNAcβ1-3Galβ1-4Glc, Fucα1-2Galβ1-4GlcNAcβ1-3Galβ1-4Glc; the oligosaccharides GalNAcα1-3(Fucα1-2)Galβ1-4Glc and Galα1-3(Fucα1-2) Galβ1-4Glc are preferred.

It is possible to graft onto the solid phase another type of oligosaccharides binding to antibodies present in blood samples or products obtained from blood other than those that are capable of binding to anti-determinant A, B, H antibodies of the blood groups. Examples of oligosaccharides of this type that may be cited are oligosaccharides that may be involved in therapeutic issues:

xeno-antigens, of different types such as Xeno Lewis$^a$ (in particular marketed by ELICITYL, with reference GLY076), Galα1-3Galβ1-3(Fucα1-4)GlcNAc, Xeno Lewis$^x$ (in particular marketed by ELICITYL, with reference GLY075), Galα1-3Galβ1-4(Fucα1-3)GlcNAc, Xeno antigen type 2 (in particular marketed by ELICITYL, with reference GLY074-2), Galα1-3Galβ1-4GlcNAc and Xeno antigen type 1 (in particular marketed by ELICITYL with reference GLY074-1), Galα1-3Galβ1-3GlcNAc.

Forssman antigens, in the form of a pentaose (in particular marketed by ELICITYL, with reference GLY132) GalNAcα1-3GalNAcβ1-3Galα1-4Galβ1-4Glc or a triaose (in particular marketed by ELICITYL, with reference GLY133) GalNAcα1-3GalNAcβ1-3Gal.

During the preparation of the substrates used in the context of the invention, the oligosaccharides must be functionalized in order to allow them to be grafted onto the solid phase by covalent bonding, by reaction on an aldehyde function present at the surface of the solid phase.

An example of a functionalization of this type is the presence of an amine function of the type —NH$_2$, —NH—NH$_2$, or —O—NH$_2$.

In addition, advantageously, in order to prepare a substrate used in the context of the invention, molecules of oligosaccharide(s) are grafted onto a solid phase carrying free aldehyde functions —CHO by reaction on only a portion of the free aldehyde functions —CHO present on the solid phase, of an oligosaccharide carrying a reactive function that is capable of forming a covalent bond with said aldehyde function —CHO. The covalent bond existing between the solid phase and the molecules of oligosaccharides grafted onto the final substrate will thus result from this reaction on a portion of the free aldehyde functions —CHO initially present. Preferably, the molecules of oligosaccharide are grafted onto the solid phase by reaction of a functionalized oligosaccharide carrying an amine function of the —NH$_2$, —NH—NH$_2$, or —O—NH$_2$ type, optionally in the protected form, and an aldehyde function —CHO carried by the solid phase before grafting.

To this end, it is possible to use an oligosaccharide carrying an amine function, a protected amine (in the form of trifluoroacetate or Boc, in particular). It is also possible to introduce a function of this type by starting from an oligosaccharide carrying a halogenated function (by carrying out a Gabriel reaction, for example) or from an oligosaccharide that has reacted with a hydrazine or from one of its derivatives, or an activated oligosaccharide for "click chemistry". It is also possible to functionalize the oligosaccharide by reducing amination with a reagent carrying an amine function or hydrazine function and optionally another function that could be derivatized subsequently.

Such functions could, for example, be introduced by "click chemistry" using oligosaccharides carrying an allyl function and in particular a —N(COCH$_3$)—CH$_2$—CH=CH$_2$ function on the anomeric carbon, position 1 of the sugar in the reducing position obtained by a bacterial fermentation process, in particular as described in Application WO 01/04341, reference to which should be made in order to obtain further details. This function may also be introduced onto the native oligosaccharide by reaction of an amine, for example propargylamine, on the aldehyde of the oligosaccharide and stabilization of the intermediate by acetylation in order to form a —N(COCH$_3$)—CH$_2$—CH=CH$_2$ function.

An amine function could be introduced onto the oligosaccharide by reaction with a reagent carrying an amine function at one end and a function that is capable of reacting on the allyl function carried by the oligosaccharide at the other end. A function of this type will, for example, be a thiol function —SH, a conjugated diene (by the Diels-Alder reaction). It is also possible to carry out an ozonolysis on the allyl function followed by a reducing amination with ammonia.

An amine function may also be introduced by a "click chemistry" reaction carried out by reaction on an oligosaccharide carrying a —C≡CH function, in particular propargyl. This propargyl function could be introduced during the production of the oligosaccharide by a fermentation pathway using the process described in Application WO 01/04341, to which reference should be made in order to obtain further details. This function may also be introduced onto the native oligosaccharide by reaction of an amine, for example propargylamine, on the aldehyde of the oligosaccharide and stabilization of the intermediate by acetylation in order to form a —N(COCH$_3$)—CH$_2$—CCH function.

In this case, a "click chemistry" reaction will be carried out with a reagent carrying firstly an azide-N$_3$, thiol —SH function, for example, and secondly an amine type function. The reaction between a —C≡CH function and —N$_3$ function leads to the formation of a triazole group. The reaction between a —C≡CH function and one or two —SH functions respectively result in the formation of one or two thioether(s).

Different coupling arms could be present in said reagent (used to graft the oligosaccharide) between the function intended to establish the link with the oligosaccharide (in particular —SH, —N$_3$) and the function (in particular amine of the type —NH$_2$, —NH—NH$_2$, or —O—NH$_2$) that will subsequently be used to carry out the covalent grafting of the oligosaccharide onto the solid phase: in particular, coupling arms of the polyethylene glycol type or in fact alkylene chains of the —(CH$_2$)$_m$— type in which m may in particular be 2, 3, 4, or 5.

The quantity of functionalized oligosaccharide(s) reacted on the solid phase will be adjusted so as to obtain a substrate with the desired degree of grafting and a ratio of free aldehyde functions present on the solid phase after grafting/molecules of oligosaccharide(s) grafted onto the solid phase within the desired ranges. In particular, a sufficiently low quantity will be used so that the aldehyde functions present on the solid phase are not saturated.

Advantageously, in the substrates used in accordance with the invention, the ratio of the number of molecules of oligosaccharide(s) grafted onto the solid phase/number of free aldehyde functions present on the solid phase is in the range 1/400 to 1/1, preferably in the range 1/200 to 1/10, and/or the substrate comprises 1 to 100 mg of oligosaccharide(s)/g of substrate, preferably between 2 and 40 mg of oligosaccharide(s)/g of substrate.

Reference should be made to the examples for the method of assaying the grafted oligosaccharide or oligosaccharides and for the calculation of the quantity of oligosaccharide(s) grafted per gram of substrate as well as the method of assaying the free aldehyde functions and the calculation of the ratio of the number of molecules of oligosaccharide(s) grafted onto the solid phase/number of free aldehyde functions present on the solid phase that may be used.

During the preparation of the substrates used in the context of the invention, grafting of the functionalized oligosaccharide(s) is usually carried out on the solid phase that is taken up in suspension in a solvent. Grafting is generally carried out in suspension in an aqueous solvent by reducing amination. To this end, the solid phase carrying free aldehyde functions is taken up into suspension in a buffer, in particular slightly acidic (for example with a pH of 6-7) in the presence of an oligosaccharide functionalized with an amine function of the —NH$_2$, —NH—NH$_2$, or —O—NH$_2$ type and a reducing agent that does not reduce the free aldehyde functions not reacting with the amine functions. The reaction between the —NH$_2$ functions and a portion of the free aldehyde functions forms an unstable imine intermediate. This imine is reduced by the reducing agent to provide a covalent —CH$_2$—NH— bond. In general, the reaction will be carried out at a temperature of the order of 20° C. to 30° C., with stirring for 2 to 10 hours. An example of a selective reducing agent that may be cited is sodium cyanoborohydride. The term "selective reducing agent" means a reducing agent that stabilizes the imine function formed without reducing the free aldehyde functions that have not reacted with the amine functions. As an example, a powerful reducing agent such as sodium borohydride (NaBH$_4$) would not be appropriate because it would also reduce all of the residual free aldehyde functions present on the solid phase.

Coupling reactions of this type are known for proteins and could be applied by analogy: reference could in particular be made to Immunology, 1971, 20, 1061. A Simple Method for Coupling Proteins to Insoluble Polysaccharides, C. J. SANDERSON and D. V. WILSON, for grafting onto the solid phase.

Finally, on the substrate used in the context of the invention, the covalent oligosaccharide/solid phase link could be established via various spacer arms in particular including a triazole group or a —S— bond and/or a polyethylene glycol chain and/or several alkylene chains that are identical or different of the —(CH$_2$)$_m$— type, in which m may be 2, 3, 4, or 5 in particular. In particular, an arm defined in the oligosaccharide-solid phase sense of the type —N(COCH$_3$)—CH$_2$—CH$_2$—CH$_2$—S—(CH$_2$)$_p$— in which p could be 2, 3, 4, or 5, could be used. This arm may be obtained from an oligosaccharide carrying an allyl function; this is easily purified after fermentation and has an arm that is relatively easy to synthesize.

In particular, in the substrates used in accordance with the invention, the molecules of oligosaccharide are grafted onto the solid phase via a spacer arm —NH-L- in the solid phase-oligosaccharide sense, and in particular —CH$_2$—NH-L-. In particular, the spacer arm L comprises a triazole group or a —S— bond and/or a polyethylene glycol chain and/or one or more alkylene chains that are identical or different of the —(CHO$_2$)$_t$— type, in which t may be 2, 3, 4, or 5, for example. In particular, the spacer arm L corresponds to the concatenation: —CH$_2$—CH$_2$—S—CH$_2$—CH$_2$—CH$_2$—N(COCH$_3$)—, the group N(COCH$_3$) being directly bonded to a saccharide unit of the oligosaccharide, preferably to the anomeric carbon of said saccharide unit.

After grafting the oligosaccharides, the substrate does not undergo any treatment that could affect the free character of the residual aldehyde functions. In particular, the residual aldehyde functions present on the solid phase after grafting of the oligosaccharides do not undergo any reduction or blocking reactions so they remain in their free —CHO form.

Figure 2:
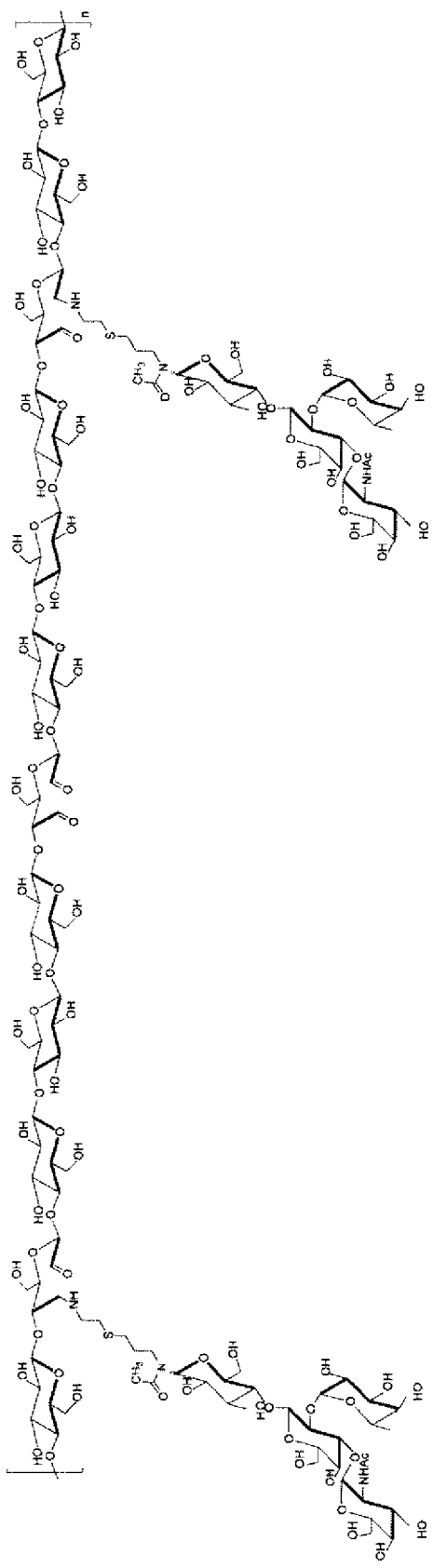
FIG. 2 presents a cellulose in accordance with FIG. 1 onto which several molecules of two oligosaccharide examples have been grafted (blood group A antigen tetraose type 5 with a spacer arm which comprises a -S- linker).
Figure 3:
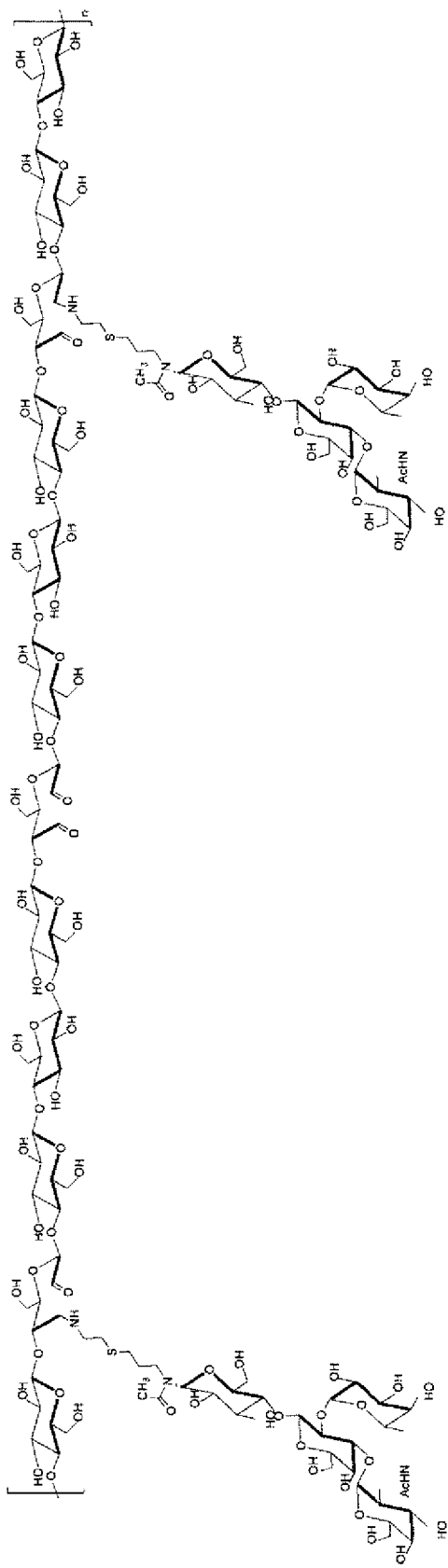
FIG. 3 presents another cellulose in accordance with FIG. 1 onto which several molecules of two oligosaccharide examples have been grafted (chemically modified blood group A antigen tetraose type 5 with a spacer arm which comprises a -S- linker).

In the context of the invention, a substrate is used wherein the solid phase carries both residual free aldehyde functions and grafted molecules of oligosaccharide(s). FIGS. 2 and 3 present a cellulose in accordance with FIG. 1 onto which several molecules of two oligosaccharide examples have been grafted. Here again, the alternation of grafting onto an aldehyde function, absence of grafting and grafting onto another aldehyde function presented in FIGS. 2 and 3 is given purely by way of illustration. The grafting could be regular or random and separated by any distance. In contrast, in the substrates in accordance with the invention wherein the solid phase has a saccharide structure such as cellulose in which the aldehyde functions have been obtained by periodic oxidation, there will be molecules of oligosaccharide(s) grafted onto an oxidized saccharide unit still carrying a free aldehyde function. In fact, grafting two oligosaccharides onto two free aldehyde functions of the same open saccharide unit of the solid phase is not favourable. In addition, the neighboring aldehyde of an open saccharide unit carrying an oligosaccharide is most usually free. Such a configuration will stabilize the oligosaccharide/antibody bond.

In accordance with a preferred embodiment, in the substrates used in the context of the invention, the solid phase is cellulose that, before grafting the molecules of oligosaccharide, comprises units with formula:

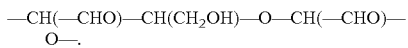

After grafting, in the substrates used in the context of the invention, the solid phase is preferably cellulose that comprises units with formula:

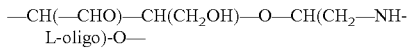

and/or units with formula:

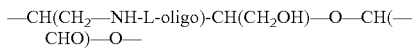

in which L is a spacer arm and oligo is an oligosaccharide that is capable of binding to one or more antibodies, preferably an oligosaccharide that is capable of binding to anti-determinant A, B, or H antibodies of blood groups.

However, the exemplary examples carried out on substrates of the methacrylic polymer type having free aldehyde functions introduced in a more random manner show that such a configuration, although favourable, is not strictly necessary in order to obtain the stabilization of the oligosaccharides/antibodies bond; the presence of free aldehyde functions distributed over the substrate is sufficient.

When preparing the substrates used in the context of the invention, in contrast to that which is conventionally carried out for coupling, particularly of proteins (A Simple Method for Coupling Proteins to Insoluble Polysaccharides, C. J. SANDERSON and D. V. WILSON, Immunology, 1971, 20, 1061), passivation of the remaining free aldehyde functions, in particular by reduction, is not carried out. In fact, in the context of the invention, as will become clear from the examples, it has been shown that the presence of residual free aldehyde functions means that the affinity bond generated between the oligosaccharides and the antibodies to which they are bound is stabilized. The substrate is used for the purification of a biological liquid corresponding to whole human or animal blood or to a product obtained from human or animal blood containing antibodies to be captured, in which said biological liquid is brought into contact with the at least said substrate in order to ensure stabilization of the bond to the antibodies, and in particular IgGs, which bind to at least certain of the molecules of oligosaccharide(s) grafted to the surface of the solid phase. In particular, the stabilization is ensured by means of at least a portion of the free aldehyde functions present on the solid phase, which interact with said antibodies linked by affinity binding to an oligosaccharide. In particular, at least a portion of the aldehyde functions interact with an asparagine, lysine, arginine, glutamine, tryptophan, tyrosine or cysteine present on said antibodies in order to form a covalent bond.

Purification Process

The substrates described above in the context of the invention could be used in any immunoaffinity technique, for example by chromatography or by adsorption onto a suspension of substrate (routinely known as a batch mode) applied to a biological liquid corresponding to whole human or animal blood or to a product obtained from human or animal blood comprising antibodies. The substrates in accordance with the invention can be used to purify any type of biological liquid containing antibodies for which the oligosaccharide or oligosaccharides present on the substrate have an affinity. The substrate in accordance with the invention will enable the antibodies that will bind to the molecules of oligosaccharide(s) grafted to the solid phase of the substrate used in the context of the invention to be extracted.

The biological liquid could correspond to a biological liquid obtained from a single individual or to a mixture of different biological liquids, preferably of the same nature (a pool of plasma, for example) obtained from different individuals, and in particular from different human beings. Unless otherwise specified, the term "whole human or animal blood" thus means whole blood obtained from a single human or animal individual or a mixture of whole blood obtained from different individuals, preferably from different human beings. Similarly, the term "product obtained from human or animal blood" thus means a product obtained from blood originating from a single human or animal individual or a mixture of products obtained from blood originating from different individuals, preferably from different human beings.

The term "product obtained from blood" in particular means a serum, a blood plasma (i.e. the liquid portion of the blood constituted by water, mineral salts, organic molecules (proteins, lipids, glucides) in which red blood cells, leukocytes and platelets are suspended) or a plasma or serum fraction, in particular an IgG plasma fraction obtained from a single individual or obtained from different individuals. In particular, the method in accordance with the invention could be carried out on a biological liquid that is a plasma from an individual with blood group A, B, or O or a mixture of plasma from different individuals.

The invention is particularly well suited to the purification of whole blood or a product obtained from blood, in particular by selected a solid phase onto which molecules of oligosaccharide(s) are grafted that can capture the antibodies of the blood groups present.

Preferably, a substrate described in the context of the invention is used that carries molecules of oligosaccharide(s) that are capable of binding to anti-determinant A antibodies in order to purify blood from group B or products obtained from blood with group B and a substrate described in the context of the invention carrying molecules of oligosaccharide(s) that are capable of binding to anti-determinant B antibodies in order to purify blood from group A or products obtained from blood from group A. In accordance with one embodiment, the biological liquid corresponding to whole human or animal blood or to a product obtained from human or animal blood comprising antibodies contains anti-A antibodies and/or anti-B antibodies and is brought into contact with at least one substrate described in the context of the invention selected in a manner such as to obtain the capture of anti-A antibodies and/or anti-B antibodies present in the biological liquid by binding with at least certain of the molecules of oligosaccharide(s) grafted onto the solid phase.

In accordance with a particular embodiment, the biological liquid that is whole human or animal blood or a product obtained from human or animal blood comprising antibodies is brought into contact, sequentially or simultaneously, with at least two different substrates described in the context of the invention: one carrying molecules of oligosaccharide(s) that are capable of binding to anti-determinant A antibodies but not carrying an oligosaccharide that is capable of binding to anti-determinant B antibodies, and the other carrying molecules of oligosaccharide(s) that are capable of binding to anti-determinant B antibodies but not carrying an oligosaccharide that is capable of binding to anti-determinant A antibodies.

In order to purify the pools of plasma or plasma with group O, either two types of substrates described in the context of the invention is used: one carrying molecules of oligosaccharide(s) that are capable of binding to anti-determinant A antibodies in order to eliminate the anti-A antibodies, and the other carrying molecules of oligosaccharide(s) that are capable of binding to anti-determinant B antibodies in order to eliminate anti-B antibodies; or a substrate described in the context of the invention carrying both molecules of oligosaccharide(s) that are capable of binding to anti-determinant A antibodies and molecules of oligosaccharide(s) that are capable of binding to anti-determinant B antibodies.

In accordance with a particular implementation of the purification method in accordance with the invention:
the biological liquid is whole blood from group A;
the biological liquid is brought into contact with a substrate described in the context of the invention carrying molecules of oligosaccharide(s) that are capable of binding to anti-determinant B antibodies, in a manner such as to capture the anti-determinant B antibodies, by binding to said oligosaccharide(s).

In accordance with another particular implementation of the purification method in accordance with the invention:
the biological liquid is whole blood from group B;
the biological liquid is brought into contact with a substrate described in the context of the invention carrying molecules of oligosaccharide(s) that are capable of binding to anti-determinant A antibodies, in a manner such as to capture the anti-determinant B antibodies, by binding to said oligosaccharide(s).

In accordance with a particular implementation of the purification methods in accordance with the invention, before or after eliminating the anti-A antibodies and/or anti-B antibodies, the biological liquid is deleukocyted in order to constitute a blood preparation that is free from anti-determinant A and B antibodies.

In accordance with another particular implementation of the purification methods applied to the purification of whole blood from group O, before or after eliminating the anti-A antibodies and/or anti-B antibodies, the blood is deleukocyted in order to constitute a blood preparation that is free from both the antigenic determinants A and B and of anti-determinant A and B antibodies.

A prior step for equilibration prior to bringing the substrate described in the context of the invention into contact with the product obtained from the blood to be treated could be used, in particular a step for equilibration in a PBS type buffer or a saline buffer containing an anticoagulant (such as ACD, acid citrate dextrose or CPD, citrate phosphate dextrose), in particular at a pH in the range 5.5 to 9.5, and in particular in the range 6.4 to 7.8.

Advantageously, the substrate/biological liquid contact is carried out by placing said substrate in the biological liquid to be purified under incubation conditions allowing for oligosaccharide/antibodies binding. Preferably, after contact, said substrate is separated from the biological liquid, in particular by filtration or centrifugation.

In particular, in the case of a purification by adsorption onto a suspension of substrate described in the context of the invention, the treated biological liquid and substrate will, for example, be separated by a sedimentation or centrifugation type separation.

In the context of the invention, the contact between the substrate and the biological liquid to be purified may be carried out by taking up said at least one substrate into suspension in the biological liquid to be purified, preferably with stirring, in particular from 50 to 500 rpm and/or for a contact peroid of 3 minutes to 3 hours, and preferably equal to 1 hour and/or with a mass of substrate of 1 to 50 g per litre of biological liquid.

Preferably, said contact is carried out at a temperature in the range from 0° C. to 45° C., preferably at a temperature of 22° C.±5° C.

Said contact is preferably carried out at a pH between 6 and 8.

Said contact may be carried out in the presence of an anticoagulant (such as ACD, acid citrate dextrose or CPD, citrate phosphate dextrose).

In accordance with a preferred implementation, said contact is brought about by placing said substrate in a blood collection bag.

In accordance with another implementation, said contact is brought about by placing said at least one substrate in a column and moving the biological liquid over said at least one substrate.

In accordance with a particular implementation that is applicable to the purification of whole blood, the substrate may advantageously be integrated into a plasmapheresis circuit comprising a blood collection bag connected to a deleukocyting filter that is in turn connected to a transfer bag placed on a stirrer, the collection bag containing the substrate in sufficient quantities to carry out deleukocytation of the whole blood and capture of the antibodies simultaneously, and in particular of anti-determinant A, B, and/or H antibodies. In this implementation, the blood that has thereby been deleukocyted and purified of antibodies could be used as it is or be separated into a plasma and erythrocyte fractions.

The substrates described in the context of the invention should preferably be used as consumables in order to avoid any risk of cross-contamination between the purification of two successive biological liquids. The cost of production will clearly be commensurate with this choice of use.

In particular, the present invention proposes the use of a substrate described in the context of the invention in order to obtain blood plasma or plasma preparations for reducing the concentration of antibodies of the blood groups present to below acceptable thresholds, irrespective of whether the antibodies are of type IgG or IgM. By adjusting the nature of the oligosaccharides present and using, in combination, both at least one oligosaccharide(s) capable of binding to anti-determinant A antibodies and at least one oligosaccharide(s) capable of binding to anti-determinant B antibodies, it is possible to obtain blood plasmas or plasma preparations that are known as universal preparations because they do not present any risk upon administration to humans irrespective of their blood group, A, B, or O.

The presence of free aldehyde functions on the solid phase of the substrate used means that the oligosaccharide/antibodies linkage can be stabilized, in particular in the case of antibodies of type IgG and IgM, this stabilization possibly being more marked in the case of IgGs. This stabilization may involve bonding, in particular by covalent bonding, between an asparagine, lysine, arginine, or glutamine present on the antibody bound to an oligosaccharide and a free aldehyde function present on the solid phase of the substrate described in the context of the invention. Similarly, this stabilization may be brought about by means of an amino acid with an alkaline pKa such as tyrosine, tryptophan, or cysteine present on the antibodies and a free aldehyde function present on the solid phase of the substrate described in the context of the invention. In the case of asparagine, the micro-environment generated by binding the antibody onto the oligosaccharide favours the non-enzymatic N-glycation of a free aldehyde function located on the substrate close to the grafted oligosaccharide (and in particular the neigbouring aldehyde in the case of a cellulose type substrate comprising —CH(—CHO)—CH(CH$_2$OH)—O—CH(CH$_2$—NH-L-oligo)-O— units) onto an asparagine of the antibody. The stabilization may also be brought about by forming a Schiff base type conjugate involving an amino acid of the bound antibody comprising a free amine function, which will form a covalent bond of the —C=N— type that could be reduced in the case of a biological liquid that will have a reducing medium at the binding site for the antibody, and the bond formed will be yet more stable.

The invention is of particular application in the purification of plasma or plasma IgG fractions, for the preparation of plasma or plasma fractions containing intravenous immunoglobulins (IVIG). IVIGs are whole human immunoglobulin G therapeutic preparations obtained from plasma pools originating from several thousand healthy donors. The IgGs of which the IVIG preparations are composed have a broad spectrum of reactivities that are directed against exogenic antigens (in particular viral and bacterial), auto-antigens (natural auto-antibodies) and antibodies (anti-idtiotypical antibodies). The principal therapeutic indications concern the treatment of certain auto-immune diseases and the reduction of infectious risks, particularly in immunosuppressed patients. Because they come from large pools of donors with all of the blood groups, these immunoglobulins contain anti-determinant A and B antibodies in a sufficiently high titre to present hemolytic risks in multi-injected patients (Hemolytic anemia following IV-IgG therapy in patients treated for Kawasaki disease: a report of 4 cases. R. Berard, B. Whittemore, R. Scuccimarri—Pediatric Rheumatology 2012, 10:10).

The increase in the purification yields for the whole of this IgG fraction from plasma and the change in the donor profile means that purification of the anti-determinant A and B antibodies is vital (Strategies to Address Hemolytic Complications of Immune Globulin Infusions, *Center for Biologics Evaluation and Research, FDA, Plasma Protein Therapeutics Association (PPTA), National Heart, Lung, and Blood Institute, NIH, January* 28-29, 2014, Lister Hill Auditorium, NIH Campus, Bethesda Md.).

The purification methods in accordance with the invention are particularly suitable for the purification of intravenous immunoglobulins in order to make their therapeutic use safer. The purification may be carried out by means of the substrates described in the context of the invention, in suspension or in accordance with a protocol using a column, on the initial plasma or after obtaining precipitation fractions containing the IgG immunoglobulins.

The following examples are provided in order to illustrate the invention, but are not in any way limiting in nature.

Apparatus and Conditions Used for the Characterizations

Measurement of Absorbance

The absorbance was measured using a UNICO 1200P spectrophotometer. The sample was transferred into a specific PMMA measuring cell.

HPAEC-PAD

The monosaccharides profile was determined by HPAEC on a ICS2500 Dionex chromatographic system. The separation was carried out on a Dionex CarboPac PA1 column. Elution was carried out with a gradient of sodium hydroxide, sodium acetate and deionized water at 17° C. The elution conditions are detailed in Table 1 below:

TABLE 1

| Time (min) | NaOH 200 mM | Deionized water | NaOH 200 mM Acetate 1M |
|---|---|---|---|
| 0 | 9.0% | 91.0% | 0.0% |
| 20 | 9.0% | 91.0% | 0.0% |
| 20.1 | 7.0% | 91.0% | 2.0% |
| 35 | 0.0% | 50.0% | 50.0% |
| 35.1 | 50.0% | 0.0% | 50.0% |
| 50 | 50.0% | 0.0% | 50.0% |
| 50.1 | 9.0% | 91.0% | 0.0% |
| 65 | 9.0% | 91.0% | 0.0% |

The detection was carried out by pulsed amperometry on a gold electrode. Each monosaccharide was calibrated by means of an external calibration.

MALDI TOF

The mass spectra were obtained using a Maldi-ToF-ToF Speed mass spectrometer (Bruker Daltonics). The sample was prepared in $2\times10^{-4}$ M solution in water. 0.5 μL of the sample solution prepared with 0.5 μL of 50 mg/mL DHB (2.5-dihydroxybenzoic acid) was deposited on a plate. It was allowed to dry at ambient temperature or in a stream of air at ambient temperature. After drying the deposit, the measurement was carried out with the mass spectrometer. 10 sets of 1000 shots each were carried out at different sites of the deposit. The set of 10000 acquisitions constituted the final spectrum. The scale of masses was adjusted by passage through a "Bruker peptide calibration standard 2" calibration solution.

Proton NMR

The proton NMR spectra were acquired using a Bruker Avance III 400 MHz magnetic resonance spectrometer. The sample, in the lyophilized form, was prepared in a solution of D$_2$O in a concentration of almost exactly 5 to 10 mg in 700 μL of D$_2$O comprising an internal calibration substance, namely 1.77 g/l sodium succinate. The acquisition was carried out in a NMR tube at 80° C. with a relaxation time d1 of 20 seconds and using 16 scans. The raw acquisition data were processed using Topspin NMR software from Bruker.

Method of Assaying the Grafted Molecules of Oligosaccharide(s) and Calculation of the Quantity of Grafted Oligosaccharide(s) Per Gram of Substrate The oligosaccharide(s) degree of grafting was measured by analysis of the constituent monosaccharides after hydrolysis, for example using trifluoroacetic acid (TFA), of the substrate used in accordance with the invention resulting in total hydrolysis of the oligosaccharide. To this end, it was possible to use the following type of protocol: 20 mg of substrate in accordance with the invention was hydrolysed with 500 μL of 2N TFA for 4 h at 99° C. The mixture was then neutralized with 53 μL of 19N NaOH and adjusted to 1 mL with deionized water. A standard for the oligosaccharide in its form used for grafting or, preferably, in its non-functionalized form was treated under identical conditions. After filtration and fourfold dilution, the monosaccharide profile was determined by HPAEC-PAD. The comparison of the results obtained for the substrate in accordance with the invention and the standard on the assay of the specific saccharide units of the oligosaccharides not present in the solid phase used, in particular fucose and galactose in the case of the oligosaccharides used in the examples that are not present on the cellulose used in certain of the examples as a solid phase, leads either directly to the grafted quantity of oligosaccharide in the case in which the standard is the oligosaccharide in its non-functionalized reducing form, or to the quantity of grafted oligosaccharide+spacer arm in the case in which the standard is the oligosaccharide in its form employed for grafting. In this case, the quantity of grafted oligosaccharide may be obtained directly after deduction of the mass of the spacer arm.

Method of Assaying the Free aldehyde Functions and Calculating the Ratio of the Number of Molecules of Oligosaccharide(s) Grafted Onto the Solid Phase/Number of Free Aldehyde Functions Present on the Solid Phase The number of aldehyde functions present on the solid phase may be measured by means of colorimetric assay using 3.5-dinitrosalicylic acid (DNS) that will be reduced to 3-amino-5-nitrosalicylic acid (red compound) by the free aldehyde functions present, with an external calibration compound, for example glucose. A protocol type is given in Example 1. The quantity of aldehyde functions per unit mass of substrate is thus obtained, and more particularly for cellulose, this quantity possibly being expressed per polymeric glucose unit by assuming a glucose unit to have a molar mass of 162 g/mol in the cellulose polymer.

The assays of the grafted oligosaccharides per unit mass of substrate or per glucose substrate monomer for cellulose with respect to the assay of the aldehyde functions per unit mass of substrate or per glucose substrate monomer for cellulose can be used to determine the ratio of the number of molecules of oligosaccharide(s) grafted onto the solid phase/number of free aldehyde functions present on the solid phase.

The oligosaccharides that will be grafted are as follows:

The denomination GrA signifies that the oligosaccharide is capable of binding to anti-determinant A antibodies present in individuals with blood group B or O, and GrB signifies that the oligosaccharide is capable of binding to anti-determinant B antibodies present in individuals with blood group A or O.

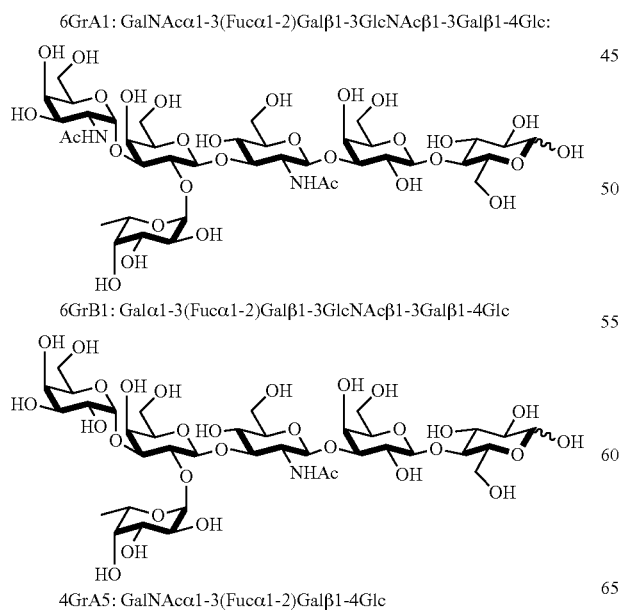

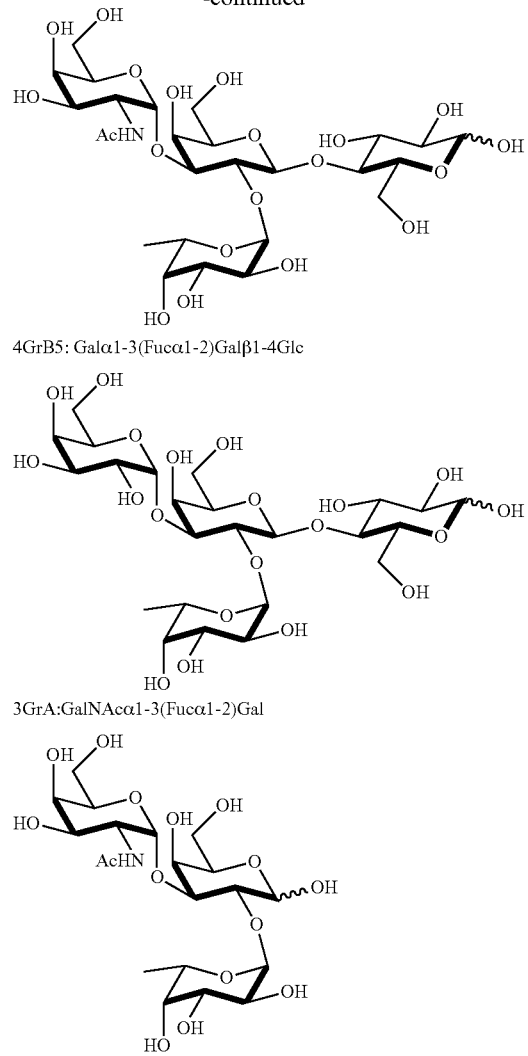

The examples below are provided in order to illustrate the invention, but are not in any way limiting in nature.

I. Preparation of Substrates

Example 1

Activation of Micronized Cellulose and Grafting of the Oligosaccharide 6GrA1-NAc-Propargyl that has been Activated with an Amine Function Micronized cellulose, Vitacel 600-30 produced by Rettenmaier, was activated by generating aldehyde functions, obtained by a treatment with the metaperiodate NaIO$_4$. To this end, 500 g of micronized cellulose was mixed with 100 g of NaIO$_4$ and 5 L of water. The mixture was kept at ambient temperature overnight, with stirring, then the cellulose substrate obtained was rinsed with water, then with ethanol and oven dried at a temperature of approximately 50° C.

The number of aldehyde functions generated on the cellulose substrate in this manner was measured by colorimetric assay of the reducing functions. To this end, 5 mg of the activated cellulose obtained was dissolved in 500 µL of deionized water. 500 µL of reagent was added to 10 g/L DNS (1.6 g of NaOH in 15 mL of deionized water, 1 g of 3.5-dinitrosalicylic acid (DNS) in 20 mL of deionized water, 30 g of potassium sodium double tartrate, adjusted to 100 mL with deionized water). After 5 minutes at 95° C., the sample obtained was cooled rapidly in cold water. 5 mL of deionized water was then added. After leaving for 20 min, the absorbance at 546 nm was read. The result obtained was compared with an external calibration curve produced under the same conditions with glucose (comprising one aldehyde per molecule). It was deduced therefrom that the activated cellulose obtained comprised 1 aldehyde function per 14 glucoses. By carrying out the assay 10 times, it appears that the precision of the measurement was 3%. The percentage precision was estimated by the ratio of the standard deviation over the mean of the measurements. The standard deviation is defined by the square root of the sum of the square of the differences from the mean divided by the number of measurements minus one.

A prior activation step for the oligosaccharide 6GrA1-NAc-Propargyl was necessary in order to allow it to be grafted onto the activated cellulose by the aldehyde functions obtained. GlycoBrick 6GrA1-NAc-Propargyl supplied by Elicityl (OligoTech Ref GLY037-1-NPR) was activated by adding an amine spacer molecule comprising a reactive azide function, a chain of 3 PEG and an amine function, 11-Azido-3,6,9-trioxaundecan-1-amine (TCI Chemical reference A2363). The GlycoBrick 6GrA1-NAc-Propargyl was dissolved in a 10 g/L methanol/water mixture (50/50) in the presence of 1.2 eq of sodium ascorbate, 0.4 eq. of $CuSO_4$ and 1 equivalent of azido amine spacer, 11-azido-3,6,9-trioxaundecan-1-amine. After approximately 2 hours with stirring, the reaction product, aminated 6AGrA1, was purified by passage over a cation exchange resin. To this end, the solution was brought into contact with Dowex® 50 resin. After elimination of the initial solution and rinsing with water, the molecule was desorbed with a 2% ammonia solution. After evaporation and freeze drying, the aminated 6GrA1 with the following formula:

quantities of water, then with pure ethanol and then dried at a temperature of the order of 50° C.

The degree of grafting of the aminated 6GrA1 was evaluated by analysis of the constituent monosaccharides after complete hydrolysis of the oligosaccharide. To this end, 20 mg of the functionalized cellulose obtained was hydrolysed with 500 µL of 2N TFA for 4 h at 99° C. The mixture was then neutralized with 53 µL of 19N NaOH and adjusted to 1 mL with deionized water. A standard aminated 6GrA1 was treated under identical conditions. After filtration and fourfold dilution, the monosaccharide profile was determined by HPAEC-PAD. The comparison of the results for the assay of the fucose and galactose specific for oligosaccharides but not present on cellulose between the grafted cellulose and the standard resulted in a grafted quantity of aminated 6GrA1 of 12.0 mg/g of final substrate, corresponding to a quantity of grafted 6GrA1 (after subtracting the mass corresponding to the spacer arm) of 9.4 mg/g of final substrate. By carrying out the assay 10 times, the precision of the measurement was determined to be 3.4%. The percentage precision was estimated by the ratio of the standard deviation to the mean of the measurements. The standard deviation is defined by the square root of the sum of the square of the differences from the mean divided by the number of measurements minus one. This corresponded to 688 moles of glucose units of the cellulose per 1 mole of grafted oligosaccharide. The number of residual aldehydes after grafting was determined using the method described in Example 1; here it was 1 in 18 (one aldehyde for 18 glucose units, the monomer for cellulose).

The ratio of the number of molecules of oligosaccharide(s) grafted onto the solid phase/number of free aldehyde functions present on the solid phase was equal to 1/38.

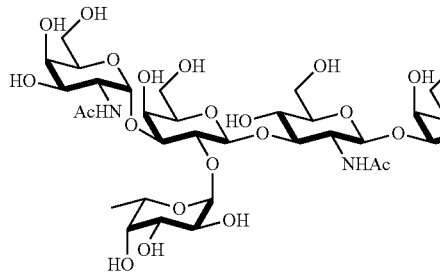
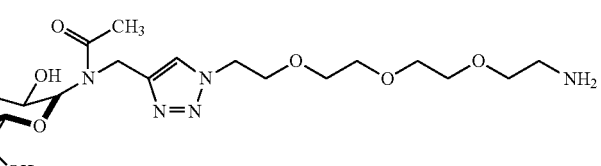

was ready to be grafted.

Grafting of the aminated 6GrA1 onto the activated cellulose obtained above was carried out as follows: 15 g of activated cellulose, 6000 µL of a solution of aminated 6GrA1 in water in an amount of 50 g/L, 2400 µL of 0.5M pH 3 phosphate buffer and 36600 mL of water were mixed for approximately 16 hours at ambient temperature. 15 mL of a solution of $NaCNBH_3$ in a concentration of 100 g/L in water was then added. It was allowed to react for 8 h with stirring. The grafted substrate was then rinsed with copious Example 2

Grafting of the Oligosaccharide 5GrB1-NAc Propargyl Activated with an Amine Function onto Pre-Activated Micronized Cellulose The pre-activated micronized cellulose produced in Example 1 was used, which comprised 1 aldehyde function per 14 glucoses.

A prior activation step for the oligosaccharide 6GrB1-NAc-Propargyl (GlycoBrick 6GrB1-NAc-Propargyl supplied by Elicityl, OligoTech® Ref GLY040-1-NPR) was carried out under the same conditions as those used in Example 1 for the oligosaccharide 6GrA1-NAc-Propargyl and produced the aminated oligosaccharide 6GrB1 with the following formula:

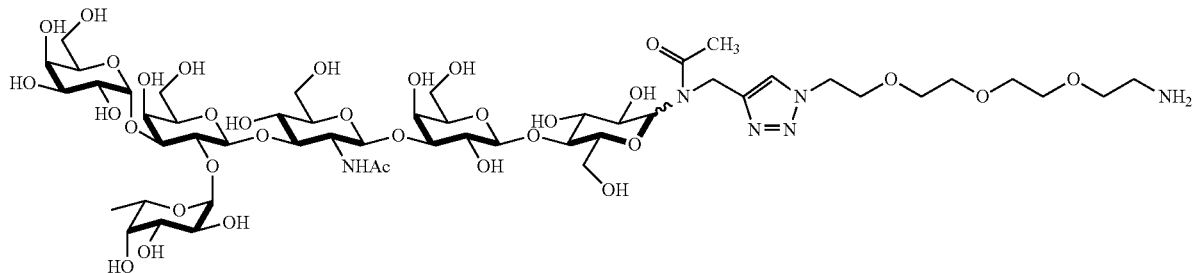

Grafting of the aminated 6GrB1 onto the activated cellulose was carried out as described in Example 1.

The degree of grafting of the aminated 6GrB1 was evaluated using the method detailed in Example 1 and was used to determine a grafted quantity of aminated 6GrB1 of 12.9 mg/g of final substrate, corresponding to a quantity of grafted 6GrB1 (after subtracting the mass corresponding to the spacer arm) of 10.0 mg/g of final substrate. This corresponded to 620 moles of glucose units of the cellulose per 1 mole of grafted oligosaccharide. The quantity of residual aldehydes after grafting was determined using the method described in Example 1; here it was 1 per 19 glucose units.

The ratio of the number of molecules of oligosaccharide(s) grafted onto the solid phase/number of free aldehyde functions present on the solid phase was equal to 1/33.

Example 3

Preparation of 4GrA5-S—(CH$_2$)$_2$—NH$_2$ and Grafting Thereof onto the Pre-Activated Micronized Cellulose 1. Preparation of Lactose-NAc-Allyl Fermentation Precursor 25 g of dehydrated lactose (Meggle DuraLac® H) was reacted with 50 mL of allylamine. After 12 hours of reaction at 43° C., stirring with a magnetic bar, the mixture was dried using a rotary evaporator under reduced pressure at 40-45° C. Co-evaporation was then carried out three times, each time with 100 mL of methanol and 100 mL of toluene. This was collectively taken up in 250 mL of methanol to which 200 mL of acetic anhydride had been added. It was allowed to react, with stirring and at ambient temperature, for 12 hours. The mixture was then dried using a rotary evaporator under reduced pressure at 40-45° C. Co-evaporation was then carried out three times, each time with 100 mL of methanol and 100 mL of toluene. The reaction mixture was taken up in 200 mL of deionized water then lyophilized. The lyophilisate was taken up in 350 mL of ethanol. The pH was adjusted to 9 with sodium methylate. It was allowed to react for approximately three hours, with stirring and at ambient temperature. Approximately 200 mL of deionized water was then added and the entirety was neutralized with hydrochloric acid.

2. Production of 4GrA5-Allyl by Fermentation

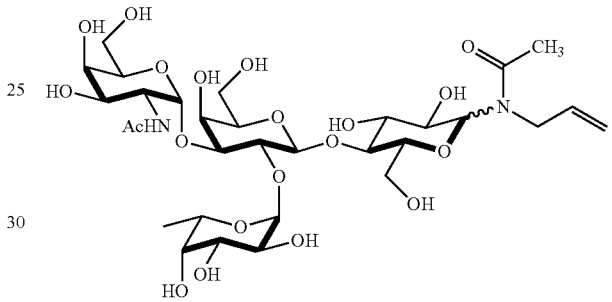

The production of 4GrA5-Allyl was carried out by providing a strain of *E. Coli* modified with allyl lactose which had already been prepared (method described in the patent FR 2 796 082). The strain producing 4GrA5 was given the reference SD142 by Elicityl (Randriantsoa, m. (2008). Synthase Microbiologique des antigenes glucidiques des groupes sanguins. [Microbiological synthesiz of glucidic antigens of blood groups]. Grenoble: thesis, Joseph Fourier University). A fermenter containing 3.7 L of culture medium (glycerol (2.4 g/L), NH$_4$H$_2$PO$_4$ (7 g/L), KH$_2$PO$_4$ (7 g/L), solution of trace minerals (7.5 mL/L), citric acid (0.6 g/L), KOH (2.5 g/L), NaOH (1 g/L), MgSO$_4$7H$_2$O (1 g/L), thiamine (4.5 mg/L)+glucose 7.5 g/L) was seeded with 80 mL of a one-day pre-culture (with an optical density of 2). The dissolved oxygen was maintained at 40%, the pH was adjusted to 6.8 by adding NH$_3$ and the temperature was kept at 34° C. The culture comprised three phases. The first phase lasted until all of the glucose had been consumed, followed by the glycerol which had initially been added to the culture medium. At the start of the second phase, the genes coding for the various synthetase and glycosyltransferase nucleotides were induced by adding IPTG (isopropyl β-D-1-thiogalactopyranoside), the substrates were added to the culture medium, and high flow rate supply (40 mL/h) was commenced, for 5 h. During the third phase, the supply flow rate was reduced to 25 mL/h. The culture was stopped 48 h after induction.

3. Purification of 4GrA5-Allyl Produced by Fermentation

The culture medium obtained above was centrifuged for 20 min at 8000 rpm. The bacterial pellet was recovered then taken up into suspension in 2 L of deionized water equivalent to the culture volume. The bacterial pellet in suspension was brought to the boil for 70 min to permeabilize the bacteria. The cellular debris was eliminated by centrifuging for 20 min at 8000 rpm. The supernatant was acidified to a pH of 3 with hydrochloric acid. The precipitate was eliminated by centrifuging for 20 min at 8000 rpm. The supernatant was neutralized with sodium hydroxide. Dowex® Optipore SD2 resin was added and it was stirred for 12 hours. After elimination of the resin, the solution was concentrated to about 500 mL in a rotary evaporator under reduced pressure. The solution was then purified using reverse phase polarity HPLC on a C18 12 μm LiChrospher substrate from Merck. Elution was carried out with a gradient of ethanol between 0 and 9% by volume. The 4GrA5-Allyl was eluted, concentrated using a rotary evaporator under reduced pressure and lyophilized. Using this purification method, 6.8 g of 4GrA5-Allyl was obtained. The identity and structure of the oligosaccharide were validated using MALDI TOF mass spectrometry and Proton NMR. The MALDI TOF mass spectrometry allowed the expected mass of 772 g/mol to be determined, i.e. 795 g/mol in its form complexed with sodium. The 1H NMR profile was in agreement with the structure. The quantitative 1H NMR with internal calibration produced an estimate of the purity as 95%±1.9%.

4. Activation of 4GrA5-Allyl by Introducing an Amine Function

Grafting of the aminated 4GrA5 onto this activated cellulose was carried out as follows: 20 g of activated cellulose, 7.530 mL of a solution of 4GrA5-S—(CH$_2$)$_2$—NH$_2$ in water in an amount of 50 g/L, 4.8 mL of phosphate buffer, 0.5M pH 3, 69.270 mL of water and 20 mL of a solution of 10 g/L NaCNBH$_3$ were mixed and stirred for about 72 h at ambient temperature. The grafted cellulose obtained was then rinsed with copious quantities of water, then with pure ethanol and finally dried under reduced pressure. 18.5 g of grafted cellulose was obtained.

The degree of grafting of the aminated 4GrA5 was evaluated using the method detailed in Example 1 and allowed a grafted quantity of aminated 4GrA5 of 16.4 mg/g of final substrate to be determined, corresponding to a quantity of grafted 4GrA5 (after subtracting the mass corresponding to the spacer arm) of 10.8 mg/g of final substrate. This corresponded to 314 moles of glucose units of the cellulose per 1 mole of grafted oligosaccharide. The quantity of residual aldehydes after grafting was determined using the method described in Example 1; here it was 1 per 15 glucose units.

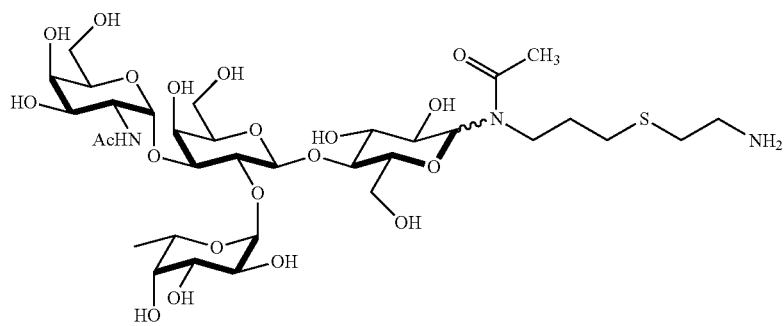

The 4GrA5-Allyl obtained above was aminated by reacting the allyl function with the thiol function of the cysteamine. To this end, 500 mg of 4GrA5-Allyl produced above was mixed with 656 mg of cysteamine and 16.3 mg of 4-cyanovaleric acid in 5 mL of deionized water. The solution is maintained for two hours with stirring at 80° C. The oligosaccharide obtained, 4GrA5-S—(CH$_2$)$_2$—NH$_2$, was then purified by passage over Dowex® 50WX4 resin. The elution was carried out with 2% ammonia. The eluted fraction was concentrated to dryness using a rotary evaporator under reduced pressure. The product was taken up in 5 mL of methanol and precipitated with 100 mL of THF. The precipitate was recovered by filtration. The product was dissolved again in 5 mL of methanol and precipitated with 100 mL of THF. The precipitate was recovered by filtration, taken up in deionized water and concentrated with a rotary evaporator and lyophilized. Using this method, 465 mg of 4GrA5-S—(CH$_2$)$_2$—NH$_2$ was obtained. The mass spectrometry MALDI TOF was used to determine an expected mass of 849 g/mol, i.e. 872 g/mol in its form complexed with sodium. The 1H NMR profile was in agreement with the structure. The quantitative 1H NMR with internal calibration produced an estimate of the purity as 100%+3.3%.

5. Coupling of 4GrA5-S—(CH$_2$)$_2$—NH$_2$ Onto Activated Cellulose

A pre-activated micronized cellulose as described in Example 1 was used, characterized by 1 aldehyde function per 12 glucoses.

The ratio of the number of molecules of oligosaccharide(s) grafted onto the solid phase/number of free aldehyde functions present on the solid phase was equal to 1/26.

Example 4

Preparation of 4GrB5-S—(CH$_2$)$_2$—NH$_2$ and Grafting Thereof to Pre-Activated Micronized Cellulose 1. Production of 4GrB5-Allyl by Fermentation

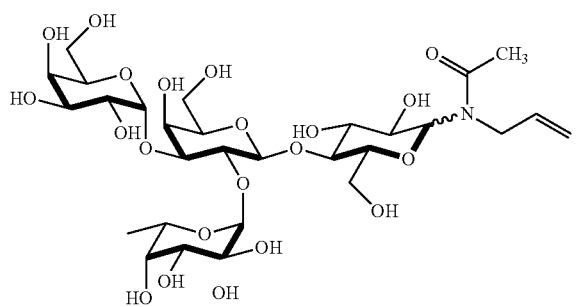

The production of 4GrB5-Allyl was carried out by providing a strain of *E. Coli* modified with allyl lactose as prepared above (method described in the patent WO 2 001 004341 A1). The strain producing the 4GrB5 was provided with the reference SD107 by Elicityl (Randriantsoa, m. (2008). Synthese Microbiologique des antigenes glucidiques des groupes sanguins. [Microbiological synthesiz of glucidic antigens of blood groups]. Grenoble: thesis, Joseph Fourier University). The procedure of Example 3-1 was followed).

2. Purification of 4GrB5-Allyl Produced by Fermentation

The purification was carried out as described in Example 3-2). Using this purification method, 6.8 g of 4GrB5-Allyl was obtained. The identity and structure of the oligosaccharide were validated using MALDI TOF mass spectrometry and Proton NMR. MALDI TOF mass spectrometry was used to determine an expected mass of 731 g/mol, i.e. 754 g/mol in its form complexed with sodium. The 1H NMR profile was in agreement with the structure. The quantitative 1H NMR with internal calibration produced an estimate of the purity as 100%±3.6%.

3. Activation of 4GrB5-Allyl by Introduction of an Amine Function after grafting was determined using the method described in Example 1; here it was 1 per 16 glucose units.

The ratio of the number of molecules of oligosaccharide(s) grafted onto the solid phase/number of free aldehyde functions present on the solid phase was equal to 1/27.

Comparative Examples 1 and 2

Reduction of Residual Aldehyde Functions Present on the Substrates of Examples 1 and 2

13 g of the grafted cellulose substrate of Example 1 or 13 g of the grafted cellulose substrate of Example 2 was suspended in 100 mL of deionized water and 300 mg of $NaBH_4$ resulting in reduction of the aldehyde functions to alcohol functions. It was stirred for 2 h at ambient temperature. Next, it was rinsed 4 times with 100 mL of deionized water, then 3 times with 100 mL of ethanol. The powder

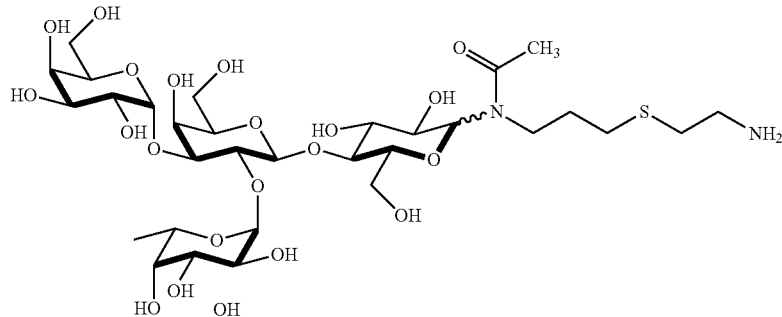

The 4GrB5-Allyl obtained above was aminated by reacting the allyl function with the thiol function of cysteamine. To this end, 500 mg of 4GrB5-Allyl produced above was mixed with 699 mg of cysteamine and 17.2 mg 4-cyanovaleric acid in 5 mL of deionized water. The solution was maintained for three hours with stirring at 80° C. The remainder of the method was as described in Example 3-3). Using this method, 461 mg of 4GrA5-S—$(CH_2)$—$NH_2$ was obtained. The identity and structure of the oligosaccharide were validated using MALDI TOF mass spectrometry and proton NMR. The MALDI TOF mass spectrometry provided the expected mass of 808, i.e. 831 in its form complexed with sodium. The NMR profile was in agreement with the structure. The quantitative NMR with internal calibration produced an estimate of the purity as 97%±4.9%.

4. Coupling of 4GrB5-S—$(CH_2)_2$—$NH_2$ Onto Activated Cellulose

A pre-activated micronized cellulose as described in Example 1 was used, characterized by 1 aldehyde function per 12 glucoses.

Grafting of the aminated 4GrB5 onto this activated cellulose was carried out as described in Example 3-4), using 7.166 mL of a solution of 4GrB5-S—$(CH_2)_2$—$NH_2$ in water in an amount of 50 g/L. 18.9 g of grafted cellulose was obtained.

The degree of grafting of the aminated 4GrB5 was evaluated using the method detailed in Example 1 and produced a grafted quantity of aminated 4GrB5 of 13.5 mg/g of final substrate, corresponding to a quantity of grafted 4GrB5 (after subtracting the mass corresponding to the spacer arm) of 9.3 mg/g of final substrate. This corresponded to 364 moles of glucose units of the cellulose per 1 mole of grafted oligosaccharide. The quantity of residual aldehydes obtained was oven dried at 50° C. for 24 h. 12.4 g of the reduced Example 1 and 12.8 g of the reduced Example 2 were respectively obtained.

The assay of the free aldehyde functions was carried out using the DNS assay method described in Example 1. The degree of grafting was determined using the HPAEC monosaccharides assay method with total hydrolysis described above.

TABLE 2

| Sample | Aldehyde functions | | Ratio, oligo of the solid phase/number of free aldehyde functions on the solid phase |
|---|---|---|---|
| | | Aminated 6GrA1* | |
| Example 1 | 1 aldehyde per 18 glucoses | 12.0 mg/g | 1/38 |
| Example 1 (after reduction) | 1 aldehyde per 327 glucoses | 11.5 mg/g | 1/2 |
| | | Aminated *6GrB1 | |
| Example 2 | 1 aldehyde per 19 glucoses | 12.9 mg/g | 1/33 |
| Example 2 (after reduction) | 1 aldehyde per 391 glucoses | 11.8 mg/g | 1/2 |

*mg of aminated oligosaccharide (aminated 6GrA1 or aminated 6GrB1)/g of substrate

Comparative Examples 3 and 4

Reduction of Residual Aldehydes on the Substrates Described in Examples 3 and 4

1 g of the grafted cellulose substrate of Example 3 or of the grafted cellulose substrate of Example 4 was suspended with 5 mL of phosphate buffer, 2M pH 7, 5 mL of deionized water and 156 mg of $NaBH_4$. It was stirred for 30 min at ambient temperature. It was then rinsed 4 times with 100 mL of deionized water, then 3 times with 100 mL of ethanol. The powder obtained was dried under reduced pressure at ambient temperature for 72 h. 870 mg of Comparative Example 3 (Example 3 with residual aldehyde function in the reduced form) and 670 mg of Comparative Example 4 (Example 4 with residual aldehyde function in the reduced form) were respectively obtained.

The assay of the free aldehyde functions was carried out using the DNS assay method described in Example 1. The degree of grafting was determined using the HPAEC monosaccharides assay method with total hydrolysis described above.

TABLE 3

| Sample | Aldehyde functions | Aminated 4GrA5* | Ratio, oligo of the solid phase/number of free aldehyde functions on the solid phase |
|---|---|---|---|
| Example 3 | 1 aldehyde per 15 glucoses | 13.1 mg/g | 1/26 |
| Comparative Example 3 (after reduction) | 1 aldehyde per 322 glucoses | 13.2 mg/g | 1/1 |
| | | Aminated *4GrB5 | |
| Example 4 | 1 aldehyde per 16 glucoses | 11.7 mg/g | 1/27 |
| Comparative Example 4 (after reduction) | 1 aldehyde per 284 glucoses | 11.6 mg/g | 1/2 |

*mg of aminated oligosaccharide (aminated 4GrA5 or aminated 4GrB5)/g of substrate

Example 5

Activation of Microcrystalline Cellulose and Grafting of the Oligosaccharide 6GrA1-NAc Propargyl that has been Activated with an Amine Function Microcrystalline cellulose, Vivapur type 101 produced by Rettenmaier, was activated by generating aldehyde functions, by treatment with metaperiodate, $NaIO_4$. To this end, 30 g of microcrystalline cellulose was mixed with 6 g of $NaIO_4$ and 300 mL of water. Mixing was maintained for 12 hours, with stirring at ambient temperature. The cellulose substrate obtained was rinsed with water, then with ethanol and oven dried at about 50° C.

The number of aldehyde functions generated in this manner on the substrate was measured by colorimetric assay of the reducing functions as described in Example 1, and resulted in 1 aldehyde function per 17 glucose units.

The oligosaccharide 6GrA1-NAc-Propargyl which had been activated by introducing an amine function (denoted aminated 6GrA1) as described in Example 1 was used for grafting.

Grafting of the aminated 6GrA1 onto the cellulose substrate which had already been activated was carried out as described in Example 1.

The degree of grafting of the aminated 6GrA1 was evaluated using the method detailed in Example 1 and resulted in a grafted quantity of aminated 6GrA1 of 9.4 mg/g of final substrate, corresponding to a quantity of grafted 6GrB1 (after subtracting the mass corresponding to the spacer arm) of 7.3 mg/g of final substrate. This corresponded to 880 moles of glucose units of the cellulose per 1 mole of grafted oligosaccharide. The quantity of residual aldehydes after grafting was determined using the method described in Example 1 and in this case was 1 per 18 glucose units.

The ratio of the number of molecules of oligosaccharide(s) grafted onto the solid phase/number of free aldehyde functions present on the solid phase was equal to 1/49.

Example 6

Activation of Microcrystalline Cellulose and Grafting of the Oligosaccharide 6GrB1-NAc-Propargyl that has Already been Activated with an Amine Function A microcrystalline cellulose which had already been activated as described in Example 5 was used, characterized by 1 aldehyde function per 17 glucoses.

The oligosaccharide 6GrB1-NAc-Propargyl activated by introducing an amine function (denoted aminated 6GrB1), as described in Example 2, was used for grafting.

Grafting of the aminated 6GrB1 onto the cellulose substrate which had already been activated was carried out as described in Example 1.

The degree of grafting of the aminated 6GrB1 was evaluated using the method detailed in Example 1 and resulted in a grafted quantity of aminated 6GrB1 of 10.3 mg/g of final substrate, corresponding to a quantity of grafted 6GrB1 (after subtracting the mass corresponding to the spacer arm) A of 8.0 mg/g of final substrate. This corresponded to 779 moles of glucose units of the cellulose per 1 mole of grafted oligosaccharide. The quantity of residual aldehydes after grafting was determined using the method described in Example 1; here it was 1 per 18 glucose units.

The ratio of the number of molecules of oligosaccharide(s) grafted onto the solid phase/number of free aldehyde functions present on the solid phase was equal to 1/43.

Examples 7 and 8

Production of Grafted Substrates at Different Concentrations of 6 GRA1 and GRB1

The pre-activated micronized cellulose produced in Example 1 was used, comprising 1 aldehyde function per 14 glucose units.

Oligosaccharides which had already been activated respectively produced in Example 1 for the aminated 6GrA1 and in Example 2 for the aminated 6GrB1 were also used.

Grafting of the aminated 6GrA1 and of the aminated 6GrB1 onto the activated micronized cellulose was respectively carried out as described in Examples 1 and 2, with the exception of the quantity of aminated oligosaccharide applied, which corresponded to that presented in Table 4 below:

TABLE 4

|  | Cellulose 6GrA1 | | | Cellulose 6GrB1 | | |
| --- | --- | --- | --- | --- | --- | --- |
|  | Ex. 7A | Ex. 7B | Ex. 7C | Ex. 8A | Ex. 8B | Ex. 8C |
| Micronized cellulose (g) | 1.25 | 1.25 | 1.25 | 1.25 | 1.25 | 1.25 |
| Aminated 6GrA1, 50 mg/mL (µL) | 500 | 250 | 125 | — | — | — |
| Aminated 6GrB1, 50 mg/mL (µL) | — | — | — | 500 | 250 | 125 |
| Phosphate buffer, 0.5M pH3 (µL) | 200 | 200 | 200 | 200 | 200 | 200 |
| Deionized water (µL) | 3050 | 3300 | 3425 | 3050 | 3300 | 3425 |
| Stirring for approximately 16 h at ambient temperature | | | | | | |
| NaCNBH$_3$, 100 g/L (µL) | 1250 | 1250 | 1250 | 1250 | 1250 | 1250 |
| Stirring for approximately 8 h at ambient temperature | | | | | | |

The grafted substrate was then rinsed with copious quantities of water, then with pure ethanol and was then dried at a temperature of the order of 50° C.

The degree of grafting of the aminated 6GrA1 and aminated 6GrB1 was evaluated using the method detailed in Example 1 and resulted in the following grafted quantities of aminated 6GrA1 and aminated 6GrB1:

TABLE 5

| Grafted substrates | Example | mg of aminated oligo/g of substrate * | mg of oligo/g of substrate ** | Ratio, oligo of the solid phase/number of free aldehyde functions on the solid phase |
| --- | --- | --- | --- | --- |
| Micronized cellulose 6GrA1 | Ex. 7A | 9.1 | 7.1 | 1/57 |
|  | Ex. 7B | 5.7 | 4.5 | 1/91 |
|  | Ex. 7C | 3.3 | 2.6 | 1/158 |
| Micronized cellulose 6GrB1 | Ex. 8A | 8.6 | 6.7 | 1/58 |
|  | Ex. 8B | 5.6 | 4.3 | 1/90 |
|  | Ex. 8C | 3.7 | 2.9 | 1/136 |

\* mg of aminated oligosaccharide (aminated 6GrA1 or aminated 6GrB1)/g of final substrate
\*\* mg of oligosaccharide (6GrA1 or 6GrB1 after subtracting the mass corresponding to the spacer arm)/g of final substrate Examples 9 and 10

Production of grafted substrates with oligosaccharides of blood groups A or B with variation 1) in the quantities of aldehyde functions present before grafting and 2) in the spacer arm used for grafting of the oligosaccharide and 3) in the size of the oligosaccharide (hexasaccharide of type 1, tetrasaccharide of type 5 or trisaccharide).

The activated micronized celluloses used were activated as in Example 1 (denoted high activation cellulose) or activated as in Example 1 with the exception that the metaperiodate was introduced in a proportion that was ten times smaller (10 g of metaperiodate per 500 g of cellulose). In this case where the cellulose was activated with less metaperiodate, a cellulose comprising 1 aldehyde function per 105 glucoses (denoted low activation cellulose) was obtained.

Various oligosaccharides of grafted blood groups sold by Elicityl were used: 6GrA1-NAc-Propargyl (OligoTech ref GLY037-1-NPR), 6GrB1-NAc-Propargyl (OligoTech ref GLY040-1-NPR), 4GrA5-NAc-Propargyl (OligoTech ref GLY035-3-NPR), 4GrB5-NAc-Propargyl (OligoTech ref GLY038-3-NPR) and 3GrA5-NAc-Propargyl (OligoTech ref GLY031-3-NPR). Each oligosaccharide was activated in the aminated form by complying with the equivalences and the operating mode described in Example 1. Only the amine/azide spacer used came in two variations: either the spacer used in Example 1 was used: (11-azido-3,6,9-trioxaundecan-1-amine-TCI Chemical reference A2363), or O-(2-aminoethyl)-O'-(2-azidoethyl)heptaethylene glycol (Aldrich ref 76318).

In the case in which the spacer used was 1 (11-azido-3,6,9-trioxaundecan-1-amine, the following was obtained:

for 6GrA1, the following aminated oligosaccharide:

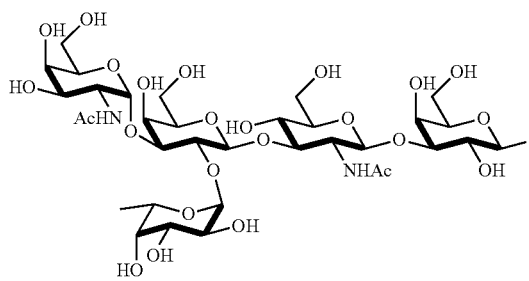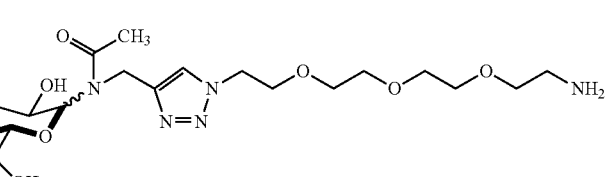

for 6GrB1, the following aminated oligosaccharide:

-continued
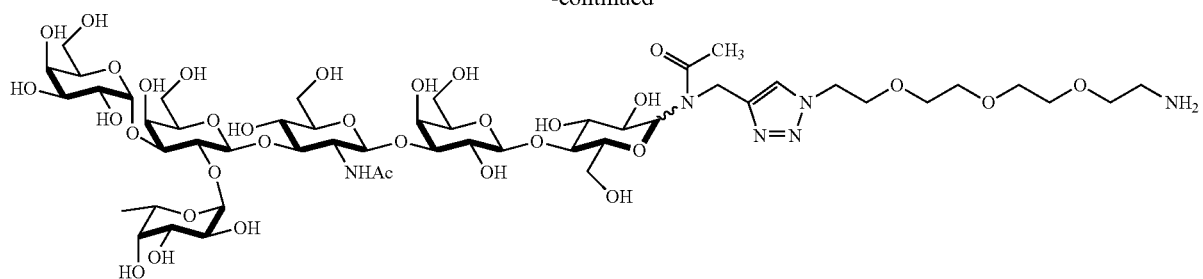
for 4GrA5, the following aminated oligosaccharide:
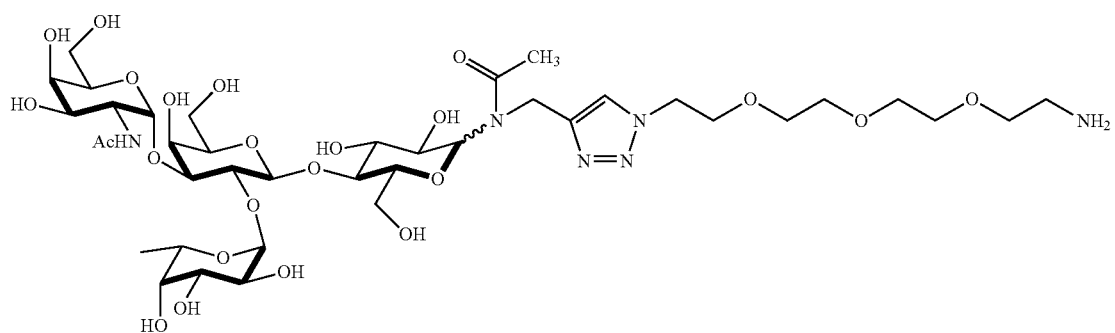
for 4GrB5, the following aminated oligosaccharide:
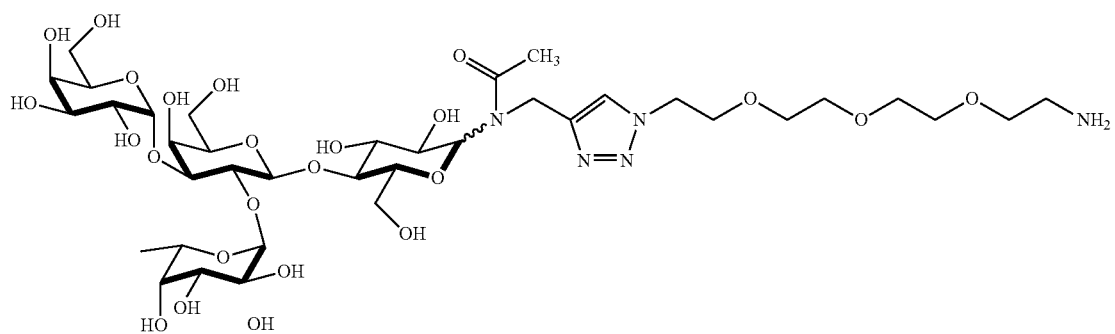
for 3GrA, the following aminated oligosaccharide:
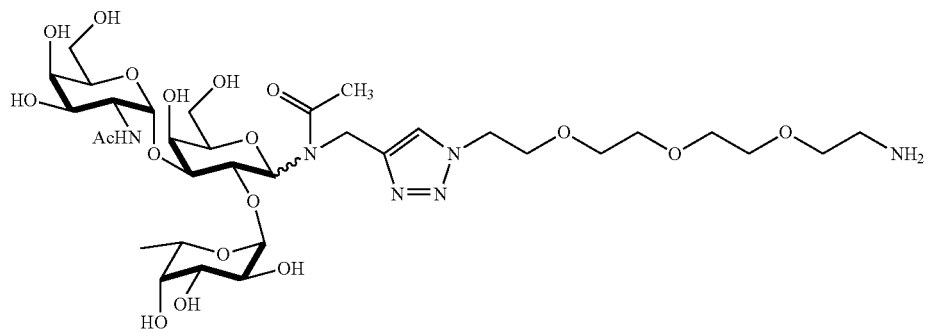

In the case in which the spacer used was O-(2-aminoethyl)-O'-(2-azidoethyl)heptaethylene glycol, the following was obtained:

for 6GrA1, the following aminated oligosaccharide:

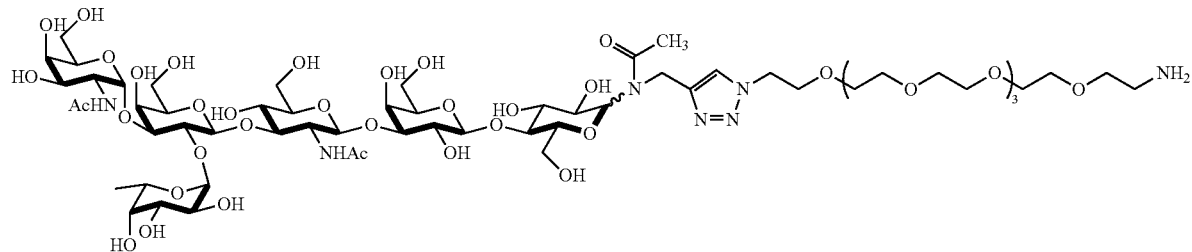

for 6GrB1, the following aminated oligosaccharide:

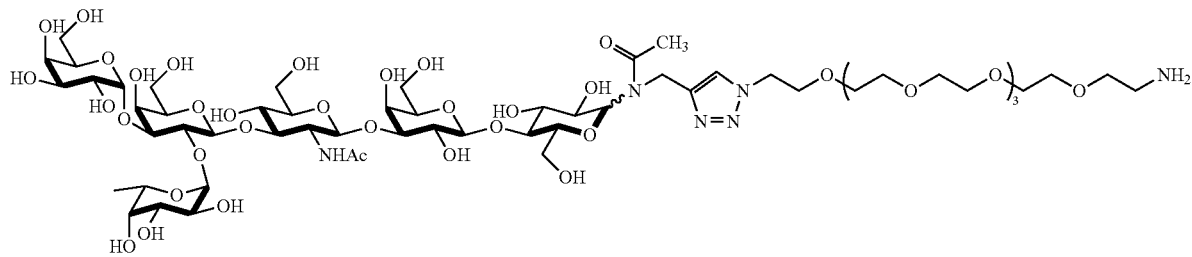

for 4GrA5, the following aminated oligosaccharide:

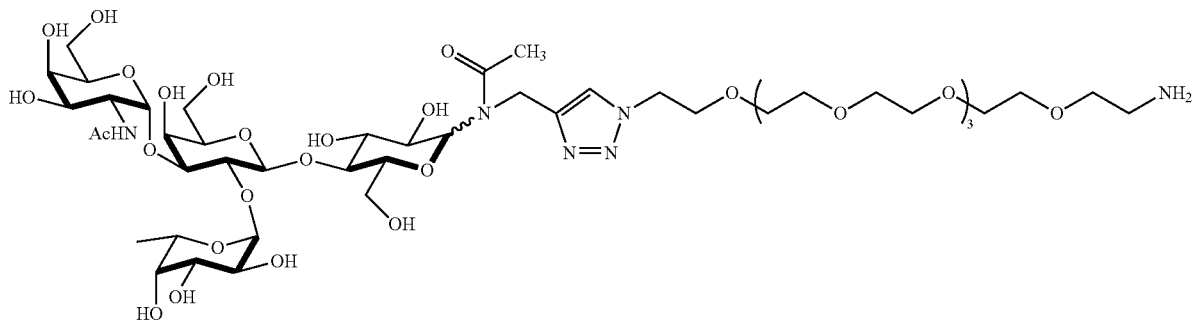

for 4GrB5, the following aminated oligosaccharide:

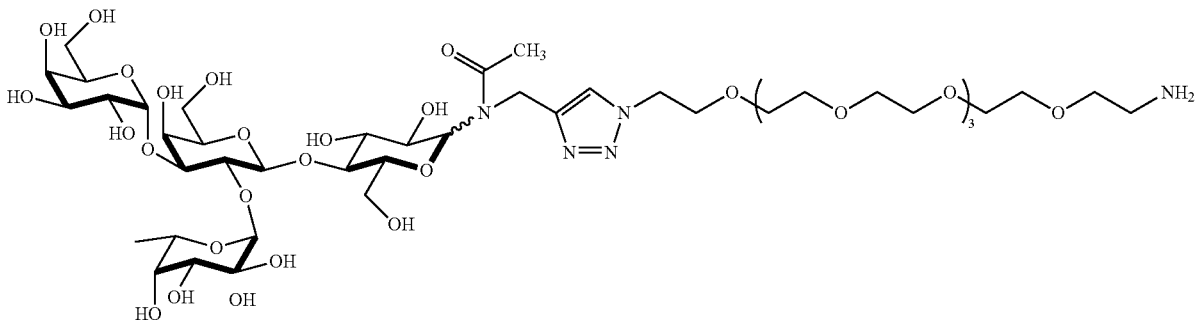

for 3GrA, the following aminated oligosaccharide:

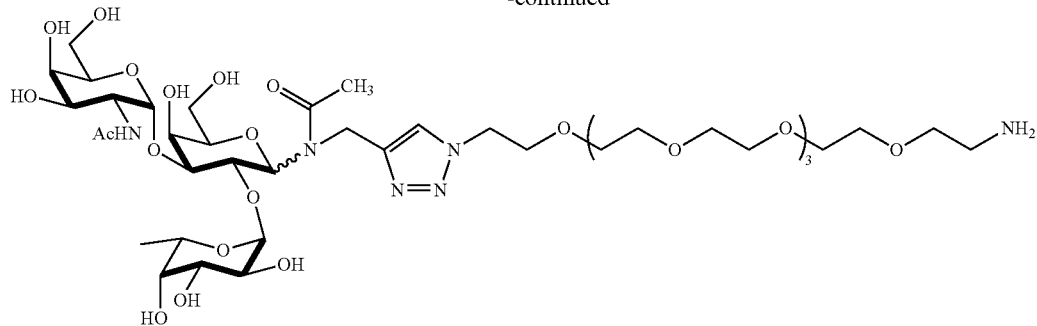

-continued

The various tests are summarized in Table 6 below:

TABLE 6

| Prepared aminated oligosaccharide | Reagents used for click chemistry | |
|---|---|---|
| | Ref for the oligo | Spacer |
| 6GrA1-Sp1-NH$_2$ | GLY037-1-NPR | 11-azido-3,6,9-trioxaundecan-1-amine |
| 6GrB1-Sp1-NH$_2$ | GLY040-1-NPR | 11-azido-3,6,9-trioxaundecan-1-amine |
| 6GrA1-Sp2-NH$_2$ | GLY037-1-NPR | O-(2-aminoethyl)-O'-(2-azidoethyl)heptaethylene glycol |
| 6GrB1-Sp2-NH$_2$ | GLY040-1-NPR | O-(2-aminoethyl)-O'-(2-azidoethyl)heptaethylene glycol |
| 4GrA5-Sp1-NH$_2$ | GLY035-3-NPR | 11-azido-3,6,9-trioxaundecan-1-amine |
| 4GrB5-Sp1-NH$_2$ | GLY038-3-NPR | 11-azido-3,6,9-trioxaundecan-1-amine |
| 4GrA5-Sp2-NH$_2$ | GLY035-3-NPR | O-(2-aminoethyl)-O'-(2-azidoethyl)heptaethylene glycol |
| 4GrB5-Sp2-NH$_2$ | GLY038-3-NPR | O-(2-Aminoethyl)-O'-(2-azidoethyl)heptaethylene glycol |
| 3GrA-Sp1-NH$_2$ | GLY031-3-NPR | 11-azido-3,6,9-trioxaundecan-1-amine |
| 3GrA-Sp2-NH$_2$ | GLY031-3-NPR | O-(2-aminoethyl)-O'-(2-azidoethyl)heptaethylene glycol |

Each aminated oligosaccharide was grafted onto one of the two activated celluloses described above using the protocol described in Example 1 and in accordance with Tables 7 and 8 below:

TABLE 7

| | Celluloses grafted with an oligosaccharide from group A | | | | | | |
|---|---|---|---|---|---|---|---|
| | Ex. 9A | Ex. 9B | Ex. 9C | Ex. 9D | Ex. 9E | Ex. 9F | Ex. 9G |
| High activation micro. cellulose (g) | 1.25 | — | 0.8 | 0.8 | 0.8 | 0.8 | 0.8 |
| Low activation micro. cellulose (g) | | 0.8 | | | | | |
| 6GrA1-Sp1-NH2 50 mg/mL (µL) | 500 | 320 | | | | | |
| 6GrA1-Sp2-NH2 50 mg/mL (µL) | | | | | 372 | | |
| 4GrA5-Sp1-NH2 50 mg/mL (µL) | | | 234 | | | | |
| 4GrA5-Sp2-NH2 50 mg/mL (µL) | | | | | | 263 | |
| 3GrA5-Sp1-NH2 50 mg/mL (µL) | | | | 195 | | | |
| 3GrA5-Sp2-NH2 50 mg/mL (µL) | | | | | | | 225 |
| Phosphate buffer 0.5M pH3 (µL) | 200 | 128 | 128 | 128 | 128 | 128 | 128 |
| Deionized water (µL) | 3050 | 1952 | 2038 | 2077 | 1900 | 2009 | 2047 |
| Stirring for approximately 16 h at ambient temperature | | | | | | | |
| NaCNBH$_3$, 100 g/L (µL) | 1250 | 800 | 800 | 800 | 800 | 800 | 800 |
| Stirring for approximately 8 h at ambient temperature | | | | | | | |

The grafted substrate was then rinsed with copious quantities of water, then with pure ethanol and was then dried at a temperature of the order of 50° C.

TABLE 8

Celluloses grafted with an oligosaccharide from group B

|  | Ex. 10A | Ex. 10B | Ex. 10C | Ex. 10D |
|---|---|---|---|---|
| High activation micro. cellulose (g) | 1.25 | — | 0.8 | 0.8 |
| Low activation micro. cellulose (g) |  | 0.8 |  |  |
| 6GrB1-Sp1-NH2, 50 mg/mL (µL) | 500 | 320 |  |  |
| 6GrB1-Sp2-NH2, 50 mg/mL (µL) |  |  |  | 374 |
| 4GrB5-Sp1-NH2, 50 mg/mL (µL) |  |  | 231 |  |
| Phosphate buffer 0.5M pH 3 (µL) | 200 | 128 | 128 | 128 |
| Deionized water (µL) | 3050 | 1952 | 2041 | 1898 |
| Stirring for approximately 16 h at ambient temperature | | | | |
| NaCNBH$_3$, 100 g/L (µL) | 1250 | 800 | 800 | 800 |
| Stirring for approximately 8 h at ambient temperature | | | | |
| The grafted substrate was then rinsed with copious quantities of water, then with pure ethanol and was then dried at a temperature of the order of 50° C. | | | | |

The degree of grafting of oligosaccharides was evaluated using the method detailed in Example 1 and resulted in the following grafted quantities of oligosaccharides:

| Grafted substrates | Example | mg of aminated oligo/g of substrate * | mg oligo/g of substrate ** | Ratio, oligo of the solid phase/number of free aldehyde functions on the solid phase |
|---|---|---|---|---|
| Grafted cellulose with oligo from Group A | Ex. 9A | 9.1 | 7.1 | 1/53 |
|  | Ex. 9B | 3.4 | 2.7 | 1/22 |
|  | Ex. 9C | 9.2 | 6.4 | 1/39 |
|  | Ex. 9D | 11.5 | 7.4 | 1/26 |
|  | Ex. 9E | 6.7 | 4.5 | 1/85 |
|  | Ex. 9F | 9.0 | 5.6 | 1/44 |
|  | Ex. 9G | 8.1 | 4.5 | 1/42 |
| Grafted cellulose with oligo from Group B | Ex. 10A | 8.6 | 6.7 | 1/55 |
|  | Ex. 10B | 4.4 | 3.4 | 1/16 |
|  | Ex. 10C | 8.9 | 6.5 | 1/38 |
|  | Ex. 10D | 6.2 | 4.1 | 1/89 |

* mg of oligosaccharide concerned/g of final substrate
** mg of oligosaccharide concerned (after subtracting the mass corresponding to the spacer arm)/g of final substrate Example 11 and Comparative Example 11

Reduced and Non-Reduced Tosoh Beads After Coupling of 4GRA5 Oligosaccharides

The grafting of the aminated oligosaccharide 4GrA5 onto the Tosoh Biosciences activated macroporous chromatographic substrate (650 AF Formyl—methacrylic polymer) having surface aldehyde functions was carried out as follows:

3 mL of Tosoh Biosciences substrate (650 AF Formyl), 18.9 mg of aminated 4GrA5 prepared as described in Example 3 and taken up in 378 µL of deionized water, 1.5 mL of phosphate buffer, 0.5M pH3 and 10 M of NaCNBH$_3$ were mixed for about 66 h at 25° C. The grafted substrate was then rinsed with copious quantities of water. 1.5 mL was preserved in order to constitute the non-reduced fraction (Example 11). Furthermore, 1.5 mL of the same grafted gel was reduced with NaBH$_4$ to a concentration of 3 mg/mL for 1 h. The operation was repeated once with 3 mg/mL of NaBH$_4$ for 1 h. The gel was then rinsed with copious quantities of water and 1.5 mL of the gel was preserved in order to constitute the reduced fraction (Comparative Example 11).

The number of aldehyde functions was measured using the DNS assay method described in Example 1. The assay was carried out using a glucose calibration expressed in µmol of aldehyde/mL, knowing that each glucose comprised one aldehyde function. The measurements were as follows:

Non-reduced gel (Ex. 11) 13.5 µmol/mL
Reduced gel (Comparative Ex. 11) 1.4 µmol/mL

| Sample | Aldehyde functions | Aminated 4GrA5 * | Ratio, oligo of the solid phase/number of free aldehyde functions on the solid phase |
|---|---|---|---|
| Example 11 | 13.5 µmol/mL | 3.2 µmol/mL | 1/4 |
| Example 11 (after reduction) | 1.4 µmol/mL | 3.1 µmol/mL | 1/1 |

* in mg of oligosaccharide concerned/g of final substrate

Example 12

Grafting onto Ultrafine Cellulose

Activation of Ultrafine Cellulose

Ultrafine cellulose, Vitacel UFC 100, produced by Rettenmaier and with ellipsoidal particles with a size of approximately 2.2 µm×8 µm, was activated by generating aldehyde functions obtained by a treatment with the metaperiodate NaIO$_4$. To this end, 150 g of micronized cellulose was mixed with 30 g of NaIO$_4$ and 1.5 L of water. Mixing was maintained at ambient temperature for 12 h, with stirring, then the cellulose substrate obtained was rinsed 4 times with 3 L of water, then 3 times with 1.5 L of ethanol and oven dried at a temperature of approximately 50° C.

Couplage of the Oligosaccharide 4GrA5-S—(CH$_2$)$_2$—NH$_2$ Onto the Activated Cellulose The Ultrafine cellulose activated as described above was used. Grafting of the aminated oligosaccharide 4GrA5 onto this activated cellulose was carried out as follows: 15 g of activated cellulose, 5.648 mL of a solution of 4GrA5-S—(CH$_2$)$_2$—NH$_2$ in water in an amount of 50 mg/mL, 3.6 mL of phosphate buffer, 0.5 M pH 3, 51.953 mL of deionized water and 15 mL of a solution of 10 mg/mL NaCNBH$_3$ were mixed and stirred for about 72 h at ambient temperature. The grafted cellulose obtained was then rinsed with copious amounts of water, twice with 200 mL, then twice with 200 mL of pure ethanol and finally dried under reduced pressure. 12.48 g of grafted cellulose was obtained (substrate A).

The degree of grafting of the aminated 4GrA5 was evaluated using the method detailed in Example 1 and allowed a grafted quantity of aminated 4GrA5 of 15.08 mg/g of final substrate to be determined, corresponding to a quantity of grafted 4GrA5 (after subtracting the mass corresponding to the spacer arm) of 9.93 mg/g of final substrate. This corresponded to 341 moles of glucose units of the cellulose per 1 mole of grafted oligosaccharide. The number of residual free aldehyde functions after grafting was determined using the method described in Example 1; here it was 1 per 18 glucose units.

The ratio of the number of molecules of oligosaccharide(s) grafted onto the solid phase/number of free aldehyde functions present on the solid phase was equal to 1/19.

Coupling of the Oligosaccharide 4GrB5-S—(CH$_2$)$_2$—NH$_2$ Onto Activated Cellulose The Ultrafine cellulose activated as described above was used. Grafting of the aminated oligosaccharide 4GrB5 onto this activated cellulose was carried out as follows: 15 g of activated cellulose, 5.375 mL of a solution of 4GrB5-S—(CH$_2$)$_2$—NH$_2$ in water in an amount of 50 mg/mL, 3.6 mL of phosphate buffer 0.5 M pH 3, 51.953 mL of deionized water and 15 mL of a solution of 10 mg/mL NaCNBH$_3$ were mixed and stirred for about 72 h at ambient temperature. The grafted cellulose obtained was then rinsed with copious amounts of water, twice with 200 mL, then twice with 200 mL of pure ethanol and finally dried under reduced pressure. 14.18 g of grafted cellulose was obtained (Substrate B).

The degree of grafting of the aminated 4GrB5 was evaluated using the method detailed in Example 1 and determined a grafted quantity of aminated 4GrB5 of 16.55 mg/g of final substrate, corresponding to a quantity of grafted 4GrB5 (after subtracting the mass corresponding to the spacer arm) of 11.40 mg/g of final substrate. This corresponded to 296 moles of glucose units of the cellulose per 1 mole of grafted oligosaccharide. The number of residual free aldehyde functions after grafting was determined using the method described in Example 1; here it was 1 per 18 glucose units.

The ratio of the number of molecules of oligosaccharide(s) grafted onto the solid phase/number of free aldehyde functions present on the solid phase was equal to 1/16.

Comparative Example 12: Reduction of Residual Aldehyde Functions on the Substrate Grafted with the Oligosaccharide 4GrA5-S—(CH$_2$)$_2$—NH$_2$ Described in Example 12

200 mg of the grafted cellulose substrate of Example 12 (substrate A or substrate B) was suspended with 250 μL of phosphate buffer, 2 M pH 8.2, and 750 μL of deionized water containing 8.26 mg of NaBH$_4$. It was stirred for 30 min at ambient temperature. It was then rinsed 3 times with 80 mL of deionized water, then twice with 25 mL of ethanol. The powder obtained was dried under reduced pressure at 50° C. for 4 h then 1 h under reduced pressure at 22° C. 189.8 mg of grafted and reduced substrate was obtained. The assay of free aldehyde functions was carried out using the DNS assay method described in Example 1. The result was 1 aldehyde per 262 glucoses, i.e. statistically, a number close to the number of glucose units per grafted oligosaccharide. The ratio of the number of oligosaccharides bound to the solid phase with respect to the number of free aldehyde functions on this solid phase was (1/341)/(1/262) i.e. 0.77.

II. Evaluation of Substrates

The plasmas before and after purification were tested using two methods:

1. The hemagglutination method, Simonin's method, a regulatory standard, which tests the agglutinating capacity of antibodies on human red blood cells from the group to be tested (A or B). This method is especially sensitive to pentameric IgMs (10 affinity sites) compared with monomeric IgGs (two reactive functions).
2. The gel test method (Lapierre Y., Rigal D., Adam J., Josef D., Meyer F., Greber S., Drot C. Transfusion. 1990 February; 30(2):109-13), which uses a miniaturized gel column containing anti IgG antibodies after contact of the red blood cells with the plasma. This method can be used to quantify the titre of IgG and IgM type antibodies. It is particularly interesting for the IgG titre.

The plasma samples before or after purification were diluted in PBS buffer by successive dilutions by a factor of 2 (1/1, 1/2_1/4096) and brought into contact with red blood cells from the blood group under consideration diluted by 1/10 in the same buffer.

The titre obtained corresponded to the last positive dilution.

A. The substrates grafted with the oligosaccharides 6GRA1 and 6GrB1 were compared as regards their efficiency for plasma purification:

3 mL of a positive plasma with 1/32 of anti-A antibodies and 1/32 of anti-B antibodies were brought into contact with 100 mg of either the substrates of Examples 1 and 2 (micronized cellulose), or 5 and 6 (microcrystalline cellulose), for 30 minutes with stirring. The test was carried out with a mixture of 50 mg of substrate A and 50 mg of substrate B i.e. respectively: substrates 1 and 2 mixed for the micronized cellulose and 5 and 6 for the microcrystalline cellulose. Purification was total for all of the substrates when the hemagglutination test was carried out.

The results show that the selected oligosaccharides are effective on the various selected cellulose substrates for plasma purification.

The same test was reproduced with 4 mL of the same plasma and 100 mg of the substrates of Examples 1, 2, 5 and 6. In this case, only the substrates from Examples 1 and 2 exhibited total absorption of the test plasma.

B. The grafted cellulose substrates of Example 1 (residual aldehyde functions in the non-reduced form) and of Comparative Example 1 (residual aldehyde functions in their reduced form), firstly and of Example 2 (residual aldehyde functions in the non-reduced form) and of the Comparative Example 2 (residual aldehyde functions in their reduced form), secondly were compared.

The tests were carried out with a plasma titrating 1/128 of anti-A antibodies and 1/128 of anti-B antibodies, with 50 mg of grafted substrate (25 mg of gel for the capture of anti-A antibodies and 25 mg of gel for the capture of anti-B antibodies) for 1 mL of plasma, with stirring for 30 minutes.

The substrates of Examples 1 and 2 (residual aldehyde functions in the non-reduced form) enabled total absorption of the plasma (of anti-A antibodies and anti-B antibodies) with a residual titre that was not detectable by the gel test and by the hemagglutination test. Thus, there was good elimination of IgMs on the two substrates for this plasma.

The substrates of Comparative Examples 1 and 2 (residual aldehyde functions in their reduced form), tested under the same conditions, each provided partial purification for the IgGs, with a residual titre of 1/32 in the gel test. Thus, it appears that the substrates in accordance with the invention carrying free aldehydes are more effective for the purification of antibodies, in particular for IgGs.

C. The grafted cellulose substrates of Example 3 (residual aldehyde functions in the non-reduced form) and of Comparative Example 3 (residual aldehyde functions in their reduced form) firstly, and of Example 4 (residual aldehyde functions in the non-reduced form) and of Comparative Example 4 (residual aldehyde functions in their reduced form) secondly were compared.

The tests were carried out with a plasma with a titre of 1/1024 of anti-A antibodies and 1/512 of anti-B antibodies as follows:

10 mg of grafted cellulose substrate of Example 3 and 10 mg of the substrate of Example 4, firstly, and 10 mg of the grafted cellulose substrate of Comparative Example 3 and 10 mg of the substrate of Comparative Example 4, secondly, were incubated for 30 minutes at 22° C. with constant stirring, in a hemolysis tube.

The results were as follows in the gel test (anti-IgG and anti-IgM detected):

| Residual titre | Anti-A antibodies | Anti-B antibodies |
|---|---|---|
| Substrate of Examples 3 and 4 | 1/16 | 1/16 |
| Reduced substrate of Comparative Examples 3 and 4 | 1/64 | 1/64 |

It appears that here again, reduction of the substrate is accompanied by a reduced efficiency in elimination of the antibodies, especially for type IgG antibodies.

D. Hemostasis results:

Three plasmas from respective groups O, A and B which had been freshly purified by absorption onto the substrates A and B corresponding to Examples 1 and 2 were inspected in respect of their hemostatic qualities. The following results were obtained between the control plasmas (ctl) and the same plasmas but purified, with the mixed substrates in accordance with the invention (test) for their anti-group A and B antibodies:

The parameters that were inspected were as follows:

FVIII c %: factor VIII coagulating activity, measured by a single-step coagulation test using the bioMerieux-deficient FVIII kit (bioMerieux, Marcy l'Etoile, France) on an MDAII instrument from bioMerieux.

FIXc %: factor IX coagulating activity, measured by a single-step test with the Biophen FactorIX kit (Hyphen-BioMed, Neuville-sur-Oise, France). vWF:AG %: von Willebrand factor antigen, test carried out with the reagents vWF AG using a BCS Coagulation Analyzer instrument (Dade Behring, Marburg, Germany). vWF:Rco %: von Willebrand activity factor, test carried out with the reagents BC vWF on a Dade Behring instrument.

FII %: percentage of plasma factor II or prothrombin, measured by a single-step test with a kit using a deficient plasma (STA deficientII, Diagnostica Stago, Asnières-sur-Seine, France).

FVII+X %: percentage of factor VII+X, measured by a single-step test with a kit using a deficient plasma (Hemoclot VII+X, Hyphen BioMed).

FV %: percentage of Factor V, measured by a single-step test with a kit using a deficient plasma (Hemoclot Factor V reagent, Hyphen BioMed).

Plasma fibrinogen: Fibrinogen, the concentration of which was measured using the Fibriquick kit (bioMerieux) based on the Clauss method.

| Plasma | FVIII c % | FIXc % | VWF: AG % | VWF: CO % | FII % | FVII + X % | FV % | Fibrinogen (g/l) |
|---|---|---|---|---|---|---|---|---|
| O test | 80.1 | 99.4 | 114.4 | 95.4 | 73 | 95 | 90 | 1.7 |
| O ctl | 90.1 | 125.4 | 109.2 | 98.4 | 70 | 106 | 107 | 2.5 |
| A test | 46.6 | 100.9 | 62.8 | 63.5 | 92 | 89 | 55 | 2.1 |
| A ctl | 50.5 | 104.1 | 61.4 | 60.7 | 103 | 88 | 56 | 2.5 |
| B test | 36.8 | 78.1 | 46.7 | 43.9 | 97 | 93 | 96 | 1.8 |
| B ctl | 37.6 | 82.9 | 44.5 | 43 | 104 | 93 | 98 | 2.0 |

These results demonstrate a very good conservation of coagulation factors after purification.

E. Influence of degree of grafting

Tests were carried out with various grafted substrates of Example 7 at various concentrations of 6 GRA1.

The tests were carried out on two 0 plasmas with high titres (1/1024 of anti-A antibodies and 1/512 of anti-A antibodies).

The incubations were carried out with 50 mg of substrate 7A, 7B or 7C using 1 mL of plasma, 30 min at 22° C. on a circular stirrer.

The purified plasmas were then tested in a gel test (with anti IgG) in order to determine the residual titre of IgG and IgM after absorption:

| Conditions for grafting | Ex. 7C | Ex. 7B | Ex. 7A |
|---|---|---|---|
| Concentrations of 6GrA1, mg/g | 3.3 | 5.7 | 9.1 |

Titres obtained after purification:

| | | | |
|---|---|---|---|
| O plasma with initial titre of anti-A antibodies of 1/1024 | 1/16 | 1/8 | 0 |
| O plasma with initial titre of anti-A antibodies of 1/512 | 1/2 | 0 | 0 |

The concentration of grafted oligosaccharides for a given mass of substrate was a determining factor for the quality of purification.

F. Comparative column and batch purification tests.

The batch purification protocol could be carried out in a chromatographic column format.

The batch tested substrates from Examples 1, 2, 5 and 6 (micronized cellulose, microcrystalline cellulose) were also deployed in a chromatographic column format.

The cellulose substrates (micronized cellulose and microcrystalline cellulose) exhibited very close chromatographic behaviors.

The tests were carried out with columns with 500 mg of gel in order to purify 5 mL of plasma.

The flow times were 14 minutes±2 minutes for all of the substrates, with a pressure of 0.1 bar.

The purification results were identical to those obtained for the batch test presented in paragraph A.

G. The substrates from Examples 3 and 4, respectively carrying the oligosaccharides 4GrA5 and 4GrB5, were tested under various incubation conditions with different times and concentrations.

The protocol was as follows:

Plasmapheresis bag tests with 10 mL of plasma (titre of anti-A antibodies 1/1024 and titre of anti-B antibodies 1/512) with a mixture containing the same quantity of grafted substrates A and B (50 mg, 100 mg or 200 mg).

The residual titres obtained were as follows:

| | Quantity of each substrate used | | | | | |
|---|---|---|---|---|---|---|
| | 50 mg | | 100 mg | | 200 mg | |
| | Titre of anti-A antibodies | Titre of anti-B antibodies | Titre of anti-A antibodies | Titre of anti-B antibodies | Titre of anti-A antibodies | Titre of anti-B antibodies |
| Incubation time 30 min | 1/8 | 1/8 | 1/4 | 1/4 | 1/2 | 1/4 |
| Incubation time 60 min | 1/4 | 1/4 | 1/2 | 1/2 | 1/2 | 0 |
| Incubation time 90 min | 1/4 | 1/2 | 1/2 | 0 | 0 | 0 |

These results show that an incubation of 1 h at a concentration of 10 mg/mL for each substrate is sufficient to purify the anti-A and anti-B antibodies to substantially below the risk threshold, the residual antibodies being IgGs.

H. Liquid phase absorption tests

In order to evaluate the performance of the prepared substrates, the cooperative effect of oligosaccharides fixed to the substrate and secondary stabilization, we incubated a high titre O plasma (1/1024 of anti-A antibodies and 1/512 of anti-B antibodies) with the same oligosaccharides as those used that were bound to the substrates, but directly in solution.

After one hour of incubating one mL of plasma with increasing concentrations of tetraose (4GrA5 and 4GrB5) and hexaose (6GrA1 and 6GrB1) oligosaccharides which had been diluted in PBS to a concentration of 100 mg/mL (i.e. 0.1 mg/μL), the quantities of oligosaccharide necessary for complete neutralization of the anti-A and B IgG and IgM antibodies of the plasma were as follows:

| Oligosaccharides | 4GrA5 | 4GrB5 | 6GrA1 | 6GrB1 |
|---|---|---|---|---|
| Volume of PBS solution used | 60 μL | 30 μL | 120 μL | 60 μL |
| Quantity of oligosaccharide used | 6 mg | 3 mg | 12 mg | 6 mg |

For the lower doses, an extended incubation of 24 h did not result in better absorption of the antibodies.

By way of comparison;
50 mg of the cellulose substrate of Example 7A carrying 0.455 mg of 6GrA1 oligosaccharides neutralized (i.e. enabled a titre of 0 to be obtained both for the anti-A and anti-B antibodies) 1 ml of the same plasma in 30 minutes, i.e. with 26 times less of oligosaccharides per millilitre of plasma than with the use of the same oligosaccharide in solution;
50 mg of the cellulose substrate of Example 8B carrying 0.287 mg of 6GrB1 oligosaccharides neutralized 1ml of the same plasma in 30 minutes, i.e. with 21 times less of oligosaccharides per millilitre of plasma than with the use of the same oligosaccharide in solution;
200 mg of the cellulose substrate of Example 3 carrying 3.28 mg of 4GrA5 oligosaccharides neutralized 10 ml of the same plasma in 90 minutes, i.e. with 18 times less of oligosaccharides per millilitre of plasma than with the use of the same oligosaccharide in solution;
200 mg of the cellulose substrate of Example 4 carrying 2.6 mg of 4GrB5 oligosaccharides neutralized 10 ml of the same plasma in 90 minutes, i.e. with 12 times less of oligosaccharides per millilitre of plasma than with the use of the same oligosaccharide in solution.

For longer incubation periods, the advantage of fixing the oligosaccharides to the substrate was even clearer.

Furthermore, liquid phase neutralization allowed immune complexes to remain in the plasma and left a very large quantity of free oligosaccharides that could have deleterious secondary effects on transfused patients.

I. Comparative Tests with Tri-, Tetra- and Hexa-Saccharides

These tests were carried out with a plasma with a titre of 1/128 anti-A and 1/8 anti-B.

The tests were carried out using a gel (gel test).

| Example | Formula of tested product | Results of gel test |
|---|---|---|
| | Anti-B antibodies | |
| Ex 10A | 6GrB1-Sp1-NH$_2$ | 0 |
| Ex 10B | 6GrB1-Sp1-NH$_2$ low activation | 0 |
| Ex 10C | 4GrB1-Sp1-NH$_2$ | 0 |
| Ex 10D | 6GrB1-Sp2-NH$_2$ | 0 |
| | Anti-A antibodies | |
| Ex9A | 6GrA1-Sp1-NH$_2$ | 0 |
| Ex9B | 6GrA1-Sp1-NH$_2$ low activation | 1/4 |
| Ex9C | 4GrA5-Sp1-NH$_2$ | 0 |
| Ex9D | 3GrA5-Sp1-NH$_2$ | 1/32 |
| Ex9E | 6GrA1-Sp2-NH$_2$ | 0 |
| Ex9F | 4GrA5-Sp2-NH$_2$ | 1/2 |
| Ex9G | 3GrA5-Sp2-NH$_2$ | 1/32 |

Conclusions:

The results for the trisaccharides were poorer than those obtained with the other oligosaccharides for the tested configurations.

There was no advantage in having a longer PEG arm: 8 as opposed to 3 ethylene glycol units.

The results for 4GR5 and 6GR1 were very close.

J. Test carried out with gels of reduced (Comparative Example 11) and non-reduced (Example 11) methacrylic polymer beads:

10 μL and 2 μL of each of the two gels obtained in Example 11 and Comparative Example 11 were incubated for one hour with rotary stirring using 1 mL of plasma with an initial titre of 1/1024 of anti-A antibodies.

The results were then evaluated using a gel test:

Residual titre of anti-A antibodies after absorption:

1. Tests with 10 μL of Gel/mL of Plasma:

| Non-reduced substrate Ex. 11 | Reduced substrate Comparative Example 11 |
|---|---|
| 1/4 | 1/8 |

2. Tests with 2 μL of Gel/mL of Plasma:

| Non-reduced substrate Ex. 11 | Reduced substrate Comparative Example 11 |
|---|---|
| 1/128 | 1/256 |

The hemagglutination test was negative for the test with 10 μL of non-reduced gel/mL of plasma, and positive for the other three tests (reduced and non-reduced gel, 2 μL of gel/mL of plasma and reduced gel, 10 μL of gel/mL of plasma). As was the case when using a cellulose type substrate, the presence of free aldehyde functions is favourable to better retention of the antibodies on the substrate, as well as for IgMs, as confirmed by the result with 10 μL of gel per mL of plasma. However, the effect was less marked than on cellulose, doubtless because of the greater rigidity of the Tosoh substrate compared with cellulose fibers and because of the smaller number of free aldehyde functions on the solid phase.

K. Example on whole blood 15 mL of collected blood on ACD (Acid citrate dextrose) anticoagulant containing 5.5 mL of plasma was brought into contact with 55 mg of the substrate of Example 3 carrying the oligosaccharide 4GrA5, in a 50 mL tube; rotary stirring was carried out at 100 rpm. After one hour of incubation at 22° C., the tube was centrifuged. After centrifugation, the cellulose substrate occupied the bottom of the tube where it formed a white, well-defined pellet above which was the pellet of red blood cells, then the leukoplatelet layer and finally the plasma.

The anti-A titre of the untreated plasma contained in the sample of whole blood was 1/128 in the gel test; it exhibited very strong agglutination in the hemagglutination test.

After treatment, the titre of plasma in the gel test was 1/8; it was negative as regards hemagglutination.

This example proves that the absorption of anti-determinant antibodies of the blood groups may be carried out on whole blood and on plasma, with a capacity to recover the blood fractions equivalent to that of untreated blood.

This absorption may be carried out directly in a bag. It may be carried out before or after deleukocyting.

L—Evaluation of the reduced and non-reduced substrates of Example 12 and of Comparative Example 12

The Ultrafine cellulose substrates grafted with the oligosaccharide 4GrA5-S—(CH$_2$)$_2$—NH$_2$ of Example 12 (free residual aldehyde functions) and of Comparative Example 12 (residual aldehyde functions in their reduced form) were compared.

The tests were carried out with 0.5 mL of plasma with a titre of 1/512 of anti-A antibodies as follows: 10 mg of grafted cellulose substrate of Example 12 firstly and 10 mg of the substrate of Comparative Example 12 secondly were incubated for 60 min at 22° C. with constant stirring in a hemolysis tube.

The direct agglutination test was negative for the non-reduced substrate and positive for the reduced substrate, meaning that the efficiency of the reduced substrate was poorer.

In the gel test, the results were as follows:

| Tested substrate | Titre of anti-A antibodies |
| --- | --- |
| Non-reduced substrate of Example 12 | 1/64 |
| Reduced substrate of Comparative Example 12 | 1/128 |

Reduction of the substrate is accompanied by a poorer efficiency for the elimination of antibodies. Under these experimental conditions, after purification using the reduced substrate, 25% of the initial antibodies remained and only 12.5% with the substrate carrying the active aldehydes.

M—Example of purification of therapeutic immunoglobulins

Immunoglobulins purified from a pool of human plasma constitute a plasma fraction of major therapeutic interest in the treatment of autoimmune diseases and for the reduction of risks of infection in immunosuppressed patients.

These purified antibodies, sold under the generic term of IVIG (Intravenous immunoglobulins), represent the total IgG fraction of plasma proteins. They contain anti-A and B antibodies of the blood groups in a sufficiently high titre to give rise to hemolytic risks in multi-injected patients. Increasing the purification yield for this IgG plasma fraction and changing the donor profile renders anti-A and B purification indispensable.

The substrates prepared in Example 12 were used for such a purification. The tests were carried out with a commercial batch of IVIG (PRIVIGEN from CSL-Behring). The titres per gel test for this preparation with 10% of immunoglobulins were respectively 1/128 of anti-A and 1/32 of anti-B.

First Test

Test Conditions:

5 mg of substrate A and 5 mg of substrate B prepared in Example 12 were incubated for 30 min with 200 μL of the undiluted commercial preparation. After centrifuging, the titre of the supernatant was measured.

Results:

The titres per gel test for this 10% preparation of immunoglobulins after absorption were respectively 1/16 of anti-A and 1/4 of anti-B, i.e. an elimination of 87.5% of anti-A and anti-B antibodies.

Second Test

Test Conditions:

50 mg of substrate A and 50 mg of substrate B prepared in Example 12 were combined in a column (column 4 g, Telos UK). A volume of 10 mL of the immunoglobulin solution diluted to 1/5 in physiological solution (PBS) was passed over the column in 30 min at 22° C.

The anti-A and anti-B titres of the filtrate were measured.

Results:

The titres per gel test for this preparation with 2% of immunoglobulins after absorption were respectively 1/1 for anti-A and 1/1 for anti-B, i.e. an elimination of more than 95% of anti-A and anti-B antibodies.

The substrates prepared in accordance with Example 12 were thus highly effective for the purification of immunoglobulin preparations.

This purification (elimination of anti-A and B antibodies of the blood groups) may be carried out on a column with results comparable to those obtained in the liquid phase with the substrate in suspension and with stirring.

N—Biological neutrality of the substrates

The two substrates prepared in Example 12 were tested as regards their specificity, in order to show that only anti-blood groups A and B antibodies are eliminated from the therapeutic immunoglobulin preparations.

The tests were carried out on the solid phase alone (activated Ultrafine cellulose of Example 12) and on the two substrates A and B grafted with the corresponding oligosaccharides of the same example.

The solution of immunoglobulin (IVIG) used in paragraph M above was treated under the following conditions after dilution to 2% in PBS:

1—Test solid phase alone (activated cellulose):

50 mg of activated cellulose in 1 mL of 2% IVIG. Incubation for one hour at 22° C., centrifugation, filtration. Measurement on the filtrate of the total protein concentration and the anti-A and anti-B titres. The total protein concentration of the immunoglobulins was measured on the Biophotometer plus instrument from Eppendorf (D) at 260, 280 and 340 nm. The results were adjusted for the immunoglobulins using the manufacturer's software. The titre was measured by the gel test (Biorad CH).

2. Test on Finished Substrates:

10 mg of substrate A and 10 mg of substrate B in 1 mL of 2% IVIG. Incubation for one hour at 22° C., centrifugation, filtration.

Measurement on the filtrate of the total protein concentration and the anti-A and anti-B titres.

Results:

1. Solid Phase Alone

|  | Protein concentration | anti-A titre | anti-B titre |
| --- | --- | --- | --- |
| Test before treatment | 17.41 mg/mL ± 0.27 | 1/32 | 1/16 |
| Test after treatment | 17.40 mg/mL ± 0.26 | 1/32 | 1/16 |

2. Test on Substrate A+Substrate B

|  | Protein concentration | anti-A titre | anti-B titre |
| --- | --- | --- | --- |
| Test before treatment | 18.50 mg/mL ± 0.28 | 1/32 | 1/16 |
| Test after treatment | 18.40 mg/mL ± 0.27 | 0 | 0 |

The first test indicates that the solid phase alone with 1 aldehyde function for fewer than 18 glucoses and a large overload of cellulose (X5) does not bind immunoglobulin by itself.

The second test shows that the slight reduction in protein concentration is consistent with the specific elimination of anti-A and anti-B antibodies and only these antibodies.

The oligosaccharide substrates defined in this manner, with free aldehyde functions in a large excess with respect to the concentration of grafted oligosaccharide antigens are ideally adapted to the purification of plasma immunoglobulins.

The invention claimed is:

1. A purification method for purifying a biological liquid comprising antibodies corresponding to whole human or animal blood or to a product obtained from human or animal blood, by bringing a biological liquid into contact with at least one substrate comprising a solid phase onto which molecules of at least one oligosaccharide that is capable of binding to one or more of said antibodies present in said biological liquid are grafted by covalent bonding, in a manner such as to obtain the capture of at least a portion of said antibodies present in said biological liquid by binding with at least some of the molecules of oligosaccharide(s) grafted onto said solid phase, characterized in that said solid phase carries free aldehyde functions —CHO, which are not on the at least one oligosaccharide.

2. A purification method according to claim 1, wherein the antibodies are anti-determinant A, B, or H antibodies of blood groups.

3. A purification method according to claim 1, characterized in that the ratio of the number of molecules of oligosaccharide(s) grafted onto the solid phase/number of free aldehyde functions present on the solid phase is in the range 1/200 to 1/10.

4. A purification method according to claim 1, characterized in that the substrate comprises 1 to 100 mg of oligosaccharide(s)/g of substrate.

5. A purification method according to claim 1, characterized in that the capture of the at least portion of said antibodies is obtained by an immunological recognition by said molecules of oligosaccharides(s) grafted onto the solid phase of the antibodies, and the free aldehyde functions stabilize the antibodies following the immunological recognition by said molecules of oligosaccharide(s) grafted onto the solid phase.

6. A purification method according to claim 1, characterized in that the molecules of oligosaccharide(s) are grafted onto the solid phase via a linker resulting from the reaction of an amine function of the type —$NH_2$, —NH—$NH_2$, or —O—$NH_2$ carried by the oligosaccharide before grafting and an aldehyde function —CHO carried by the solid phase before grafting.

7. A purification method according to claim 1, characterized in that the solid phase is a polysaccharide and the free aldehyde functions result from a periodic oxidation.

8. A purification method according to claim 1, characterized in that the solid phase is cellulose.

9. A purification method according to claim 8, characterized in that the grafted cellulose comprises units with formula:

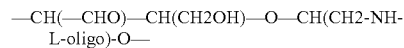

and/or units with formula:

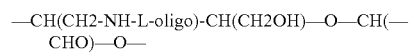

in which L is a spacer arm and oligo is the oligosaccharide that is capable of binding to one or more antibodies.

10. A purification method according to claim 1, characterized in that the molecules of oligosaccharide are grafted onto the solid phase via a spacer —NH-L- in the solid phase-oligosaccharide direction, L being a spacer arm.

11. A purification method according to claim 9, the spacer arm L comprises at least one of a triazole group, a -S- linker and/or a polyethylene glycol chain and/or one or more identical or different alkylene chains.

12. A purification method according to claim 9, characterized in that the oligosaccharide comprises saccharide units and the spacer arm L corresponds to a concatenation:

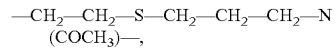

the group N(COCH$_3$) being bonded directly to a saccharide unit of the oligosaccharide.

13. A purification method according to claim 1, characterized in that the oligosaccharide is a trisaccharide, a tetrasaccharide, a pentasaccharide or a hexasaccharide, and the antibodies are anti-determinant B antibodies or anti-determinant A antibodies.

14. A purification method according to claim 1, characterized in that characterized in that the oligosaccharide is selected from GalNAcα1-3(Fucα1-2)Galβ1, Galα1-3(Fucα1-2)Galβ1, GalNAcα1-3(Fucα1-2)Galβ1-4Glc, Galα1-3(Fucα1-2)Galβ1-4Glc, GalNAcα1-3(Fucα1-2)Galβ1-3GlcNAβ1-3Galβ1-4Glc, Galα1-3(Fucα1-2)Galβ1-3GlcNAβ1-3Galβ1-4Glc, GalNAcα1-3(Fucα1-2)Galβ1-4GlcNAcβ1-3Galβ1-4Glc, Galα1-3(Fucα1-2)Galβ1-4GlcNAcβ1-3Galβ1-4Glc, Fucα1-2Galβ1-3GlcNAc, Fucα1-2Galβ1-4GlcNAc, Fucα1-2Galβ1-4Glc, Fucα1-2Galβ1-3GlcNAcβ1-3Gal, Fucα1-2Galβ1-4GlcNAcβ1-

3Gal, Fucα1-2Galβ1-3GalNAcβ1-3Gal, Fucα1-2Galβ1-3GlcNAcβ1-3Galβ1-4Glc, and Fucα1-2Galβ1-4GlcNAcβ1-3Galβ1-4Glc.

15. A purification method according to claim 1, characterized in that after contact, said substrate is separated from the biological liquid.

16. A purification method according to claim 14, characterized in that characterized in that the biological liquid is a plasma from an individual with blood group A, B, or O or a mixture of plasmas from different individuals.

17. A purification method according to claim 1, characterized in that the biological liquid is whole blood.

18. A purification method according to claim 1, characterized in that the biological liquid comprises antigenic determinants A and B and anti-determinant A and B antibodies and the capture of at least a portion of said antibodies present in said biological liquid comprises eliminating the anti-determinant A antibodies and/or anti-determinant B antibodies and in that before or after eliminating the anti-determinant A antibodies and/or anti-determinant B antibodies, the biological liquid is deleukocyted in order to constitute a blood preparation that is free from both the antigenic determinants A and B and of the anti-determinant A and B antibodies.

19. A purification method according to claim 1, characterized in that the biological liquid is brought into contact, sequentially or simultaneously, with at least two different said substrates: one carrying molecules of oligosaccharide(s) that are capable of binding to anti-determinant A antibodies but that do not carry an oligosaccharide that is capable of binding to anti-determinant B antibodies, and the other carrying molecules of oligosaccharide(s) that are capable of binding to anti-determinant B antibodies but that do not carry an oligosaccharide that is capable of binding to anti-determinant A antibodies.

20. A purification method according to claim 1, characterized in that said at least one oligosaccharide is capable of binding to anti-Forssman antigens.

21. A purification method according to claim 1, characterized in that said contact is brought about in the presence of an anticoagulant.

22. A purification method according to claim 1, characterized in that said at least one substrate is used to ensure, by means of at least a portion of the free aldehyde functions present on the solid phase, stabilization of the antibodies that will become bound to at least certain of the molecules of oligosaccharide(s) grafted to said solid phase.

23. A purification method according to claim 1, characterized in that said contact is brought about by placing said substrate in a blood collection bag.

24. A purification method according to claim 1, characterized in that said contact is brought about by placing said at least one substrate in a column and causing the biological liquid to move over said at least one substrate.

25. A purification method according to claim 9, the spacer arm L comprises one or more identical or different alkylene chains.

26. A purification method according to claim 1, characterized in that said at least one oligosaccharide is capable of binding to anti-xenoantigen antibodies.

27. A purification method according to claim 5, wherein the free aldehyde functions stabilize the antibodies by covalent bonding of an asparagine, lysine, arginine, or glutamine present on the antibody onto a free aldehyde function present on the solid phase.

* * * * *